United States Patent [19]
Hu et al.

[11] Patent Number: 6,073,041
[45] Date of Patent: Jun. 6, 2000

[54] PHYSIOLOGICAL CORRECTIONS IN FUNCTIONAL MAGNETIC RESONANCE IMAGING

[75] Inventors: Xiaoping Hu, St. Paul, Minn.; Tuong Huu Le, Dallas, Tex.; Todd B. Parrish, Minneapolis, Minn.; Peter W. Erhard, Gauting, Germany

[73] Assignee: Regents of the University of Minnesota, Minneapolis, Minn.

[21] Appl. No.: 09/000,169
[22] PCT Filed: Jul. 18, 1996
[86] PCT No.: PCT/US96/11891
  § 371 Date: May 11, 1998
  § 102(e) Date: May 11, 1998
[87] PCT Pub. No.: WO97/04330
  PCT Pub. Date: Feb. 6, 1997
[51] Int. Cl.[7] .................................................. A61B 5/055
[52] U.S. Cl. .......................... 600/410; 600/411; 600/509; 600/534; 324/309
[58] Field of Search ..................................... 600/410, 413, 600/411, 419, 508, 509, 529, 534; 324/306, 307, 309

[56] References Cited

PUBLICATIONS

Noll et al, Theory, Simulation, and Compensation of Physiological Motion Artifacts in Functional MRI, Proceedings pf the International Conference on Image Processing, IEEE, pp. 40–44, Nov. 1994.

Hu et al "Reduction of Signal Fluctuation in Functional MRI Using Navigator Echoes", Magnetic Resonance in Medicine, vol. 31, No. 5, pp. 495–503, May 1994.

Bandettini, P.A., et al., "Processing Strategies for Time–Course Data Sets in Functional MRI of the Human Brain", Magnetic Resonance in Medicine, No. 2, pp. 161–173, (Aug. 30, 1993).

Hu, X., et al., "Retrospective Estimation and Correction of Physiological Fluctuation in Functional MRI", MRM, No. 34, pp. 201–212, (1995).

Kim, W.S., et al., "Extraction of Cardiac and Respiratory Motion Cycles by Use of Projection Data and Its Applications to NMR Imaging", Magnetic Resonance in Medicine, No. 1, pp. 25–37, (Jan. 13, 1990).

Primary Examiner—Ruth S. Smith
Attorney, Agent, or Firm—Schwegman, Lundberg, Woessner & Kluth, P.A.

[57] ABSTRACT

A functional magnetic resonance imaging method comprises the steps of:
(a) detecting a physiological timing profile;
(b) measuring cerebral k-space data to provide cerebral k-space data;
(c) ordering the measured cerebral k-space data into a unit cycle based on the detected physiological timing profile;
(d) estimating effects on individual k-space points resulting from physiological effects by non-linear least-square fitting to provide estimated physiological effects; and
(e) removing the estimated physiological effects from the cerebral k-space data by substraction of the estimated physiological effects from said k-space data.

10 Claims, 30 Drawing Sheets

PHYSIOLOGICAL CORRECTIONS IN FUNCTIONAL MAGNETIC RESONANCE IMAGING

TECHNICAL FIELD

This invention relates to improved magnetic resonance imaging techniques.

BACKGROUND

A recent development in magnetic resonance imaging (MRI) is functional magnetic resonance imaging (fMRI). fMRI relies on the detection of localized changes in signal intensity in $T2^*$-weighted (or T2-weighted) images. For example, MRI may non-invasively map human cortical function without the use of exogenous contrast agents by relying on the blood oxygenation level dependent (BOLD) contrast due to the ability of deoxyhemoglobin to act as an endogenous paramagnetic contrast agent. Therefore, changes in the local concentration of deoxyhemoglobin within the brain lead to alterations in the magnetic resonance signal. Regional neuronal activation within the cerebral cortex leads to an increase in blood flow without a commensurate increase in oxygen extraction. Consequently, the capillary and venous deoxyhemoglobin concentrations decrease, leading to a localized increase in $T2^*$ and T2. This increase is reflected as an elevation of intensity in $T2^*$-weighted and T2-weighted MR images. With its high contrast, $T2^*$-weighted imaging is the predominant technique currently employed. It was initially applied to delineate the activity in the human visual cortex, motor cortex, and areas in the frontal cortex during speech.

Although application of fMRI in delineating cortical activity in the last few years has been remarkable, ideally, only intensity changes related to neuronal activation should be detected. In practice, many other sources contribute to image-to-image intensity fluctuation, leading to artifacts in the resultant functional maps. Thus, motion artifacts continue to be a major hindrance to the accurate detection of neuronal activity.

Sources of motion artifacts include system instability, subject movement, as well as normal physiological motions. Artifacts due to gross subject motion have been recognized as one possible source of false activation, and spatial registration of images can be beneficial in reducing these artifacts. Gross involuntary subject motion can be minimized by physically constraining the subject. Other physiology related motions, such as brain motion, respiration, and cardiac pulsation, are more difficult to compensate for and cannot be eliminated in a straightforward manner. These types of motion and their effects will be referred to as physiological fluctuation or physiological effect.

SUMMARY OF THE INVENTION

The invention is a technique for removal of signal fluctuation due to physiological factors such as (but not limited to) respiration and cardiac pulsation. The technique comprises simultaneous measurement of physiological motion, such as respiration-related abdominal motion or cardiac pulse or both, during fMRI data acquisition; then, in post processing steps, imaging data are retrospectively ordered into unit physiological cycles (e.g., respiratory and cardiac cycles), after which the physiological effects are estimated and removed from the fMRI data.

A preferred embodiment involves extraction of the physiological profiles directly from the fMRI data; therefore, no external monitoring of physiology is required. The latter approach avoids problems associated with measurement of physiological parameters disturbing the static magnetic field and also the fMRI signal unless proper filtering (through a filter plate) or special fiber connections are utilized. Moreover, direct monitoring of physiological parameters may not be readily achieved for every subject.

BRIEF DESCRIPTION OF THE DRAWING

FIG. 1b shows the time course of the magnitude of the representative k-space point of FIG. 1a.

FIG. 4b shows the time course of the magnitude of the representative k-space point of FIG. 4a.

FIG. 7b shows the time course of the phase of a representative k-space point of FIG. 7a.

FIG. 8b shows a standard deviation map derived from the original image of FIG. 8a.

FIG. 8d shows the time courses, before and after correction, of the central pixel of box 1 of FIG. 8a.

FIG. 8e shows the time courses, before and after correction, of the central pixel of box 2 of FIG. 8a.

FIG. 9b shows a standard deviation map derived from the original image of FIG. 9a.

FIG. 9d shows the time courses, before and after correction, of the representative pixel of FIG. 9a.

FIG. 13b shows the cardiac profile extracted from the image shown in FIG. 13a.

DETAILED DESCRIPTION

Figure 1A:
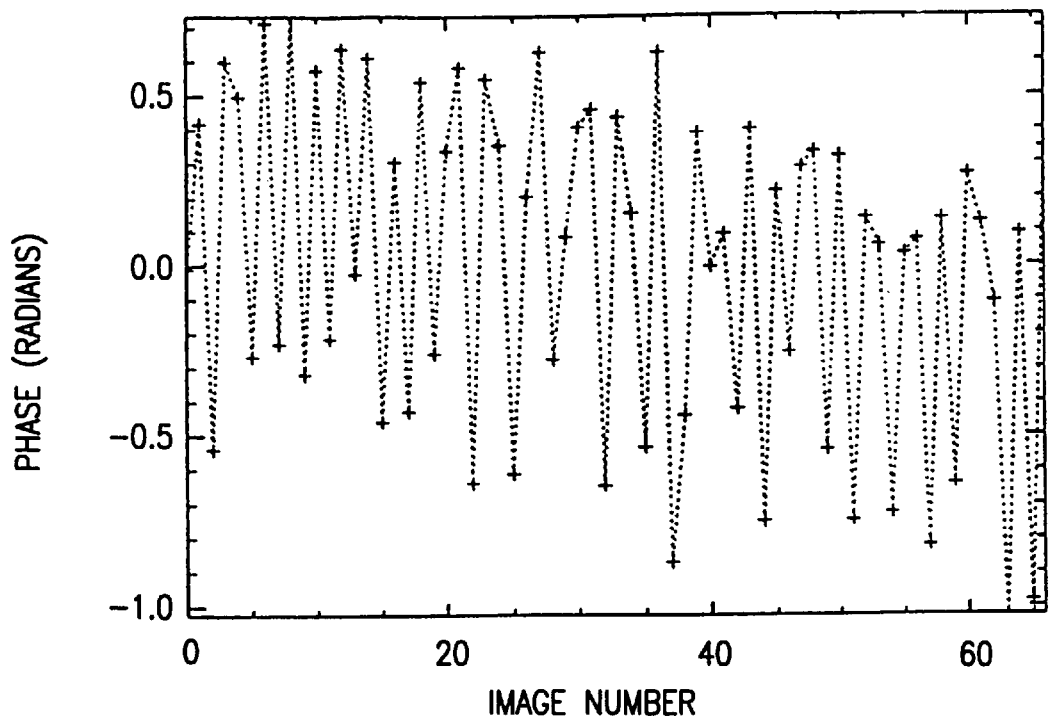
FIG. 1a shows the time course of the phase of a representative k-space point from a rapid, low flip angle pulsed NMR imaging ("FLASH") data set plotted against time.

Due to the complexity of movement of various organs associated with physiological effects such as respiration and heart beat, it is difficult, if not impossible, to describe these motions in an exact quantitative manner. The central nervous system, including the brain and the cerebrospinal fluid (CSF), pulsates due to pressure changes in the vasculature inside the cranial cavity. This pulsation has two components: (a) a relatively low amplitude and short duration displacement corresponding to cardiac pulsation; and (b) a relatively high amplitude plateau-like displacement of longer duration corresponding to respiration. The first component has been ascribed to the pressure changes in arteries, and the second has been attributed to venous pressure changes as a result of respiration. The cardiac component has been demonstrated by a number of MR studies using various techniques, and motion related to respiration has also been observed with MRI. These MR studies, as well as measurements with other modalities, are all consistent with a spatial pattern of motion. Specifically, the brain expands as a result of increased blood volume inside the cranial cavity. Since the brain tissue and the CSF are incompressible, they both tend to move downward in the direction of least resistance. However, the motion is not uniform because the brain parenchyma and the ventrides are readily deformed, and the resistance in the skull is non isotropic. For MRI, the effect of these motions are complicated. Since MRI data are acquired in the spatial frequency domain (i.e., the k-space), it is more appropriate to consider the data in the k-space for the understanding the physiological effects. The velocities of physiological brain motion are relatively small (<1 mm/sec), and they do not lead to dramatic phase changes in the measured MR signal unless a very long echo time is used. However, the positional variations due to these motions can lead to observable changes in the measured k-space data.

In addition to pulsation of the brain parenchyma and the CSF, pulsatile flow in cranial vessels, particularly arteries with relatively high velocities, also affects the MR signal. This pulsatile flow alters both the phase and the magnitude of the MR signal in the vessels. Since the k-space data correspond to integration of the signal intensity over the field of view (with linear spatial phase modulations), local fluctuations in the vessel signal lead to variations in the k-space data. In images reconstructed from such k-space data, intensity fluctuations and sometimes signal losses are present in the vessels themselves, and "ghosts" of the vessels can be found across the field of view (FOV). For fMRI these "ghosts" may lead to either "negative" intensity changes which may be erroneously interpreted as inhibition or to artifactual "activation" regions with positive changes in the brain parenchyma. Although the vascular space only comprises a small fraction of the cranial cavity, "ghosting" artifacts may be significant relative to signal changes from the BOLD effect.

Apart from movements occurring in the cranial cavity, organs in the chest and the abdomen also move as part of the physiological motions, primarily respiration. Movement of abdominal organs can affect the MR signal significantly. It has been suggested that a major consequence of such movement is an oscillation of the magnetic field in the FOV arising from the bulk magnetic susceptibility fluctuation induced by moving organs. These field changes are manifested as spatially dependent phase-modulations in gradient-echo MR signal, which lead to image dependent artifacts. Another possible consequence of gross organ movement in the chest and abdomen is the alteration of coil loading which is directly related to the measured data.

Artifacts due to physiological motion in anatomic imaging are well recognized, and an assortment of techniques have been developed for their reduction. The most straight-forward approach is to synchronize the data acquisition to the specific motion by gating or triggering. Unfortunately, synchronized acquisition cannot be used for fMRI since it will lead to variations in TR, which subsequently introduce signal fluctuations in the image unless the TR is very long. Several other techniques have been proposed to reduce physiology related signal variation in fMRI such as the navigator echo approach and the filtering approach. The navigator echo technique was originally proposed for motion artifact reduction in anatomic MR imaging and was adapted for fMRI to account for global effects of breathing. The navigator echo technique was able to reduce the signal fluctuation substantially. However, it only reduces the phase-encoding artifacts in a single image and does not directly correct the image-to-image variations. Therefore, it is not applicable to echo-planar imaging (EPI). Furthermore, since the navigator echoes can only be acquired in the absence of phase-encoding gradients, they can not fully describe the variation in each k-space point For echo-planar imaging, temporal filtering of functional images that suppresses the frequencies corresponding to the cardiac pulsation and respiration, respectively, has been described The success of the filtering approach, however, relies on the periodicity of the physiological motion and on the ability to acquire images fast relative to the physiological pulsation. To lessen the requirement on the periodicity, simultaneous physiological monitoring during the acquisition of the functional images was proposed; nevertheless, this approach, although relaxing the requirements for time invariant periodicity, still relies on short-term periodicity of the motion, a condition not always fulfilled. Furthermore, the filtering approach may distort the signal changes arising from neuronal activation.

The inventive method monitors physiological activities of the subject while functional imaging data are being acquired, and then retrospectively estimates and removes the physiological effects as guided by the acquired physiological data. The principle of retrospective extraction of the physiological signal fluctuation as applied in the invention differs from retrospective gating techniques known for cardiac MRI. Those techniques obtain cine images of the heart at different phases of the cardiac cycle without the use of cardiac triggering, which is susceptible to variations in the RR interval (i.e., the duration between consecutive R-waves of the EKG). Nor is static signal suppression is used in this invention because it is not feasible for fMRI. The inventive method relies on the phase dependence of the MR signal and utilizes it for the detection of the respiratory cycle. Extraction of the respiratory cycle from the MR signal of the brain is not known.

In obtaining the physiological profiles directly from the MR data, the invention implicitly assumes that paradigm induced signal change does not significantly affect the robustness of extracting the physiologic timing information. This assumption is valid because neuronal activation induced signal changes are relatively minute and localized to a small region. In the case of respiration, it is unlikely that the activation would significantly affect the phase of the center of the navigator echo in rapid, low flip angle pulsed NMR imaging (FLASH) or the center k-space point in EPI. As for cardiac signal extraction, it is possible that there is coupling between blood flow and neuronal activation; however, it is important to realize that only a small percentage of the vessels will be affected. Vessels located distant from the site of neuronal activation would not be affected. In the preferred embodiment of the invention as applied toe cardiac signal extraction, all locations in the projection data are searched for the best representation of the cardiac profile, thus the extracted cardiac signal is reliable. Specifically, data are acquired continuously at a fixed TR, and data for each repetition are stored along with the phase of the cardiac cycle at the time the data are acquired. The phase-encoding gradient is kept constant during each cycle and incremented when a cardiac trigger is detected. In post-processing, k-space data for each cardiac phase are calculated by interpolation. The underlying assumption is that the heart motion is reproducible at the same phase of the RR interval even though the RR interval itself could be variable.

A similar principle is applied in the invention to extract signal variation in fMRI due to physiological motion. Basically, the invention assumes that physiological effects are pseudo periodic in the sense that they can be determined to a large extent by the relative phase within a given cycle irrespective of cycle duration. Therefore, the thrust of the technique is to estimate how the signal changes in a unit cycle. This is achieved by the fitting of the repeated measurements of each k-space point, as a function of the phase within the corresponding unit cycle. In the case of respiration, the assumption of pseudoperiodicity is not always fulfilled. In that case, the assumption is relaxed such that only the functional form is assumed to be consistent in all cycles but the amplitude can change as a result of variation in breathing depth; the amplitude of the functional form is then estimated based on the measured pressure signal.

To determine the relative phase within a physiological cycle based on the time at which a k-space data point was measured, consider a complex k-space signal S(i), where i stands for image number. The same procedure is applied to each point in the k-space. Next examine the data from the physiological monitoring, e.g., the respiratory or the cardiac monitoring data, R(t) or C(t), respectively, where t represents the time points used in the sampling of the monitoring data. From the monitoring data one can also determine, T(i), the time when S(i) was acquired. In general T(i) depends on the exact location of the k-space except in the case of EPI where such dependence can be neglected.

From the physiological data, one determines the starting point, $T_s(j)$, of cycle j of the corresponding physiological motion (and consequently the ending point of the previous cycle). For example, $T_s(j)$ can be defined as the point of maximum expiration or inspiration in the case of respiration. The determination of $T_s(j)$ is accomplished with a template matching approach. The user defines a template to be matched by selecting a segment of the physiological monitoring data, and a computer program finds the points with locally maximal correlation with the template. This approach requires a negligible amount of user interaction (the selection of the template), but is fairly robust. Fully automatic approaches are also possible by using a fixed template or utilizing peak search.

Note that when the pseudoperiodicity assumption is met, the starting and ending point of each cycle can be arbitrarily chosen. This is usually the case for the cardiac pulsation but not always true for breathing. Therefore, in the example of respiration, the point of maximal expiration is used as a natural break point since the end of expiration is usually consistent in normal breathing. Consequently each respiration cycle is defined as the period between one point of maximum expiration to the next. In cases where the respiration depth is not constant, the monitored respiratory pressure is used to augment the estimation of the signal variation in each respiration cycle.

Once the physiological silhouettes have been extracted, the phase and the magnitude of individual k-space points are ordered into normalized unit cycles based on the relative time (denoted as Θ(i), where i represents the ith image) with respect to the corresponding physiological period:

$$\Theta(i) = \frac{[T(i) - T_s(j)]}{[T_s(j+1) - T_s(j)]}$$

T(i) is the time that the k-space point is sampled, and $T_s(j)$ and $T_s(j)$ are the starting and ending points of the jth physiological cycle, respectively, satisfying $T_s(j)<T(i)<T_s(j+1)$. For example, the starting and ending points of the respiratory cycle can be defined based on the time of full expiration (or peak expiration); for cardiac data, R—R intervals are conveniently identified.

Because MR data are acquired asynchronously with respect to the physiological motion, there are k-space points that are sampled before the first detectable physiological peak and those that are sampled after the last detectable peak. The relative time, Θ(i), for the k-space points collected before the first detectable peak is extrapolated based on the physiological period of the first tractable cycle:

$$\Theta(i) = \frac{[1 + T(i) - T_s(0)]}{[T_s(1) - T_s(0)]}$$

$T_s(0)$ and $T_s(1)$ are the starting and ending points of the first physiological cycle, respectively, satisfying $T(i)<T_s(0)<T_s(1)$.

Similarly, the relative time, Θ(i), for the k-space points collected after the last detectable period is:

$$\Theta(i) = \frac{[T(i) - T_s(f)]}{[T_s(f) - T_s(f-1)]}$$

$T_s(f-1)$ and $T_s(f)$ are the starting and ending points of the last physiological cycle, respectively, satisfying $T_s(f-1)<T_s(f)<T(i)$.

Once the physiologic intervals are defined, the next step is to examine temporal series of each sampled point in the k-space. Since the time at which each sample is acquired, T(i), is known, the physiological cycle it falls into can be determined as j, satisfying $T_s(j)<T(i)<T_s(j+1)$. T(i) referenced to cycle j leads to a relative time:

$$\Theta(i) = \frac{[T(i) - T_s(j)]}{[T_s(j+1) - T_s(j)]}$$

All the temporal samples of an individual k-space point can now be considered as a function of Θ(i). The measured data are retrospectively synchronized with the physiological motion.

Next, the inventive method estimates the variation in a unit physiological cycle. Since respiration is expected to affect the phase of the acquired k-space data significantly, the phase and the magnitude of the signal, instead of its real and imaginary parts, are considered. In general, the estimation is obtained with nonlinear least squares fitting, and the preferred technique is to fit the signal in a unit physiological cycle is to a truncated Fourier series:

$$f(\Theta) = A_0 + \sum_{n=1}^{N} A_n \cos(2n\pi\theta) + \sum_{n=1}^{N} B_n \sin(2n\pi\theta)$$

where $A_0$, $A_n$, and $B_n$ are coefficients to be fitted. Because unit cycle variations are relatively smooth, a second order series (i.e., N=2) is preferred (high order fitting is possible but not preferred because it was found to be unnecessary and less stable). The Fourier series ensures a periodic boundary condition. Since the object of the invention is to remove effects due to physiological variations, each fit is modified by removing a DC component corresponding to the value of the fit at the starting point (and equivalently the ending point) of the cycle.

In activation studies, it is possible that the activation related signal changes are correlated (in time) with physiological changes and may affect the estimation of unit cycle variation. As a result, the correction based on this estimation may distort the signal changes arising from neuronal activation. To avoid this problem, the estimation of unit cycle variations is obtained using the data acquired during the control period alone.

Next, the invention corrects for variations within individual cycles. For each measurement of an individual k-space data point, physiological variations in both the phase and the magnitude are predicted based on the unit cycle variation and the acquisition time relative to the corresponding physiological cycle. The estimated effects are removed from the phase and the magnitude of the measured data.

It is possible, but not preferred, to remove effects due only to a single physiological factor. When the specific physiological motions considered are both the respiratory and cardiac effects, it is preferred to estimate respiratory effects first and remove them from the original data since respiratory effects are more prominent. Subsequently, the data with respiration effects already removed are used for estimating cardiac effects. The estimated cardiac effects are then subtracted from the respiration corrected data to obtain the final result. Note that the estimation of either effect is not synchronized to the other one.

To correct for respiratory effects in cases of substantial variation in breathing depth, the unit cycle respiratory variation may be scaled by a factor calculated as the ratio of the measured pressure change in the respiration cycle over the pressure change averaged over all the cycles. The estimated respiratory effects for individual breathing cycles are then subtracted from the measured data.

In one embodiment of the invention, respiratory motion is measured using a pressure belt placed around the subject's abdomen, and cardiac pulsation is monitored with a pulse oximeter. In a preferred embodiment, however, both respiratory and cardiac timing signals are extracted directly from the MR data. Because functional imaging involves repetitive measurements, changes due to cardiac and respiratory motions are easily discernible, provided that a short repetition time is used. Various methods for obtaining physiological information directly from the MR data are known in cardiac imaging, but in most of these methods, projection-type measurements or measurements with a small amount of phase are used.

For detecting the physiological signal from FLASH data, a navigator echo is acquired in the absence of a phase encoding gradient. The navigator echo is basically the Fourier transform of a projection of the imaged slice. Because respiration affects the MR signal not only by inducing movement of the brain parenchyma but also by altering the static magnetic field, its effect is easily discernible from the phase of the center of the navigator echo. Therefore, the phase is used to depict respiratory motion. To eliminate high frequency oscillations unrelated to respiration in the phase, a digital low-pass filter with a cut-off frequency of 0.5 Hz is applied (assuming that respiratory rate does not exceed 30 cycles/min).

For EPI, the phase of the center k-space point is utilized to describe the respiratory behavior. As described above, a digital low-pass filter is also applied.

As noted before, in the case of respiration, it is unlikely that the activation would significantly affect the phase of the center of the navigator echo in FLASH or the center k-space point in EPI As for cardiac signal extraction, it is possible that there is coupling between blood flow and neuronal activation; however, it is important to realize that only a small percentage of the vessels will be affected. Vessels located distant from the site of neuronal activation would not be affected. In general, and especially for cardiac signals, all locations in the projection data should be searched for the best representation of the physiological profile to determine that the extracted physiological signal is reliable. Also, static signal suppression is not used in his invention because it is not feasible for fMRI. The inventive method relies on the phase dependence or the MR signals and utilizes it for the detection of the respiratory cycle.

Thus, the main advantages of the invention are: (a) insensitivity to changes in the duration of each physiological cycle; (b) elimination of the need for fast sampling; and (3) absence of distortion to signal arising from neuronal activity. In addition, the technique is not sequence dependent and can be used under various experimental conditions.

EXAMPLE I

Functional imaging data acquisition was accompanied by simultaneous monitoring of the respiration and cardiac signal. The respiratory signal was monitored with a flexible pressure belt placed around the upper abdomen of the subject. The cardiac signal was monitored with a pulse oximeter (NONIN, Plymouth, Minn.) placed on the finger of the subject which provides a delayed systolic signal as well as the oxygenation saturation level. A logical waveform generated by the imaging sequence indicates the time at which each MR signal is acquired. A DAS-12/50 data acquisition board with a maximum sampling rate of 50 kHz and 64 KB RAM (Analogic Co., Wakefield, Mass.) interfaced with an IBM compatible personal computer was used to sample the signal from the pressure belt, the signal from the oximeter and the logical waveform from the imager. Sampling rates between 20 to 100 Hz were used.

All MRI experiments were conducted on a 4 Tesla whole body system with a 1.25 m diameter bore, manufactured by SISCo and Siemens (SISCo. Palo Alto, Calif.; Siemens, Erlangen, Germany), and a quadrature surface coil. The magnet was equipped with a head gradient insert which produced a maximum of 3 G/cm with a rise time of 180 $\mu$s in all 3 axes. To minimize gross motion, a head molding system was used to immobilize the subject. In each experiment, T1-weighted anatomic images were first obtained with inversion-recovery prepared ultrafast gradient echo imaging and used for the identification of region of interest to be studied. Upon the localization of the region of interest, $B_0$ homogeneity was optimized.

To illustrate the performance of the new technique, consecutive T2*-weighted single-slice images were obtained under basal conditions with no neuronal task/stimulation and retrospectively processed. For FLASH, the data were acquired with a 128×128 matrix, a slice thickness of 5 mm, TR/TE of 50/35 ms, a field of view of 20×20 $cm^2$ and a flip angle of 30 degrees. Seventy images, each taking approximately 6.5 seconds, were acquired continuously. EPI data were collected with repetition times of 0.3 or 2.5 seconds, a matrix size of 64×64 and an FOV of 20×20 $cm^2$. Gradient-echo EPI with an echo time of 30 ms was used. A typical EPI data set consisted of 100–500 consecutive images.

The acquired k-space data were processed, point by point, by the retrospective technique and Fourier transformed to generate corrected images. Temporal standard deviation maps were calculated from the processed images as well as the images derived from the original data. For more detailed comparisons, average standard deviations and time courses in regions of interest (ROIs) were obtained.

In order to illustrate the utility of the retrospective correction technique, functional imaging studies were performed. The primary visual cortex of the patient was stimulated by light emitting diode goggles (Grass Instruments, Quincy, Mass.) flashing at 8 to 16 Hz. A sagittal slice 0.6 cm away from the midline was studied. Separate experiments were conducted with FLASH and EPI. FLASH images were obtained with parameters identical to those stated earlier, and EPI images were acquired with a TR of 0.3 s and other parameters described above. Each study consisted of repeated alternation between periods of light off and light on. The resultant data were retrospectively processed to remove the physiological effects. Images obtained before and after the retrospective processing were analyzed with a cross-correlation technique to generate functional activation maps at the same correlation threshold. The maps were visually examined and quantitatively compared by the area of activation detected in an ROI encompassing the visual area.

Figure 1B:
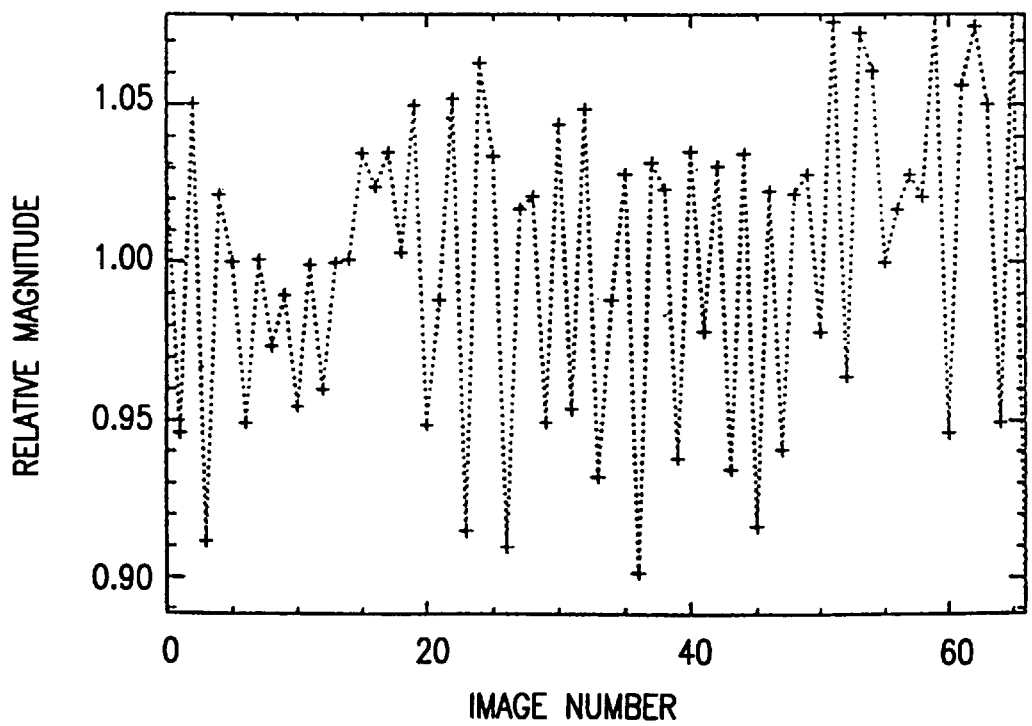

FLASH data were examined with respect to time and with respect to a unit physiological cycle. When plotted against time (image number), a representative k-space data point exhibited substantial variations in phase and magnitude, as shown in FIGS. 1(a and b), in which each data point is taken 6.5 s apart. The random fluctuation in both the phase and the magnitude of the data is apparrent from FIG. 1; however, these variations appear random since the acquisition time for each image is longer than both physiological cycles and is not synchronized with either. With the measured physiological data, a respiratory phase or a cardiac phase was assigned to each temporal sample of the k-space point based on the time at which it was detected. Subsequently, samples of the k-space point were examined as a function defined on the unit respiration cycle or the unit cardiac cycle. For the k-space data point shown in FIGS. 1(a and b), the phase and the magnitude were plotted against the respiration cycle in FIG. 2. Respiration related changes were apparent despite some scattering due to variations unrelated to breathing. The results of nonlinear fitting are shown as solid curves in FIG. 2; the variations in the data are well-characterized by the fits. Samples of a k-space data point containing substantial cardiac variation (with the respiratory effects already removed) are plotted versus the cardiac cycle in FIGS. 3(a and b) with the nonlinear fits shown as solid curves. These examples indicate that it is possible to retrospectively estimate signal fluctuations although the imaging time is much longer than both of the physiological cycles.

Figure 4A:
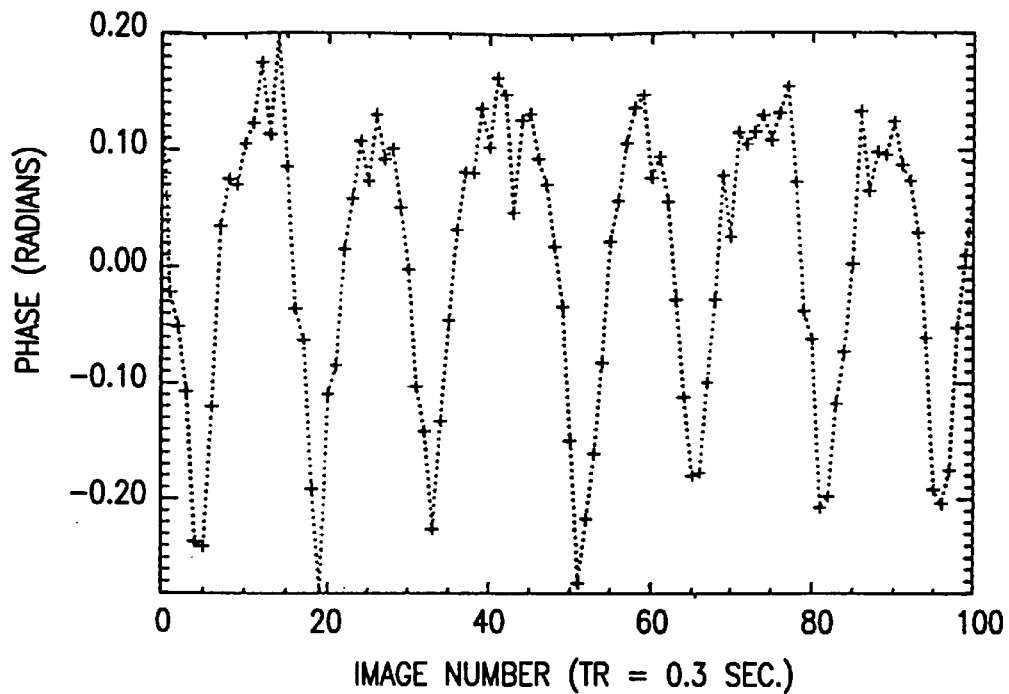
FIG. 4a shows the time course of the phase of a representative k-space point from a FLASH data set plotted against time.
Figure 4B:
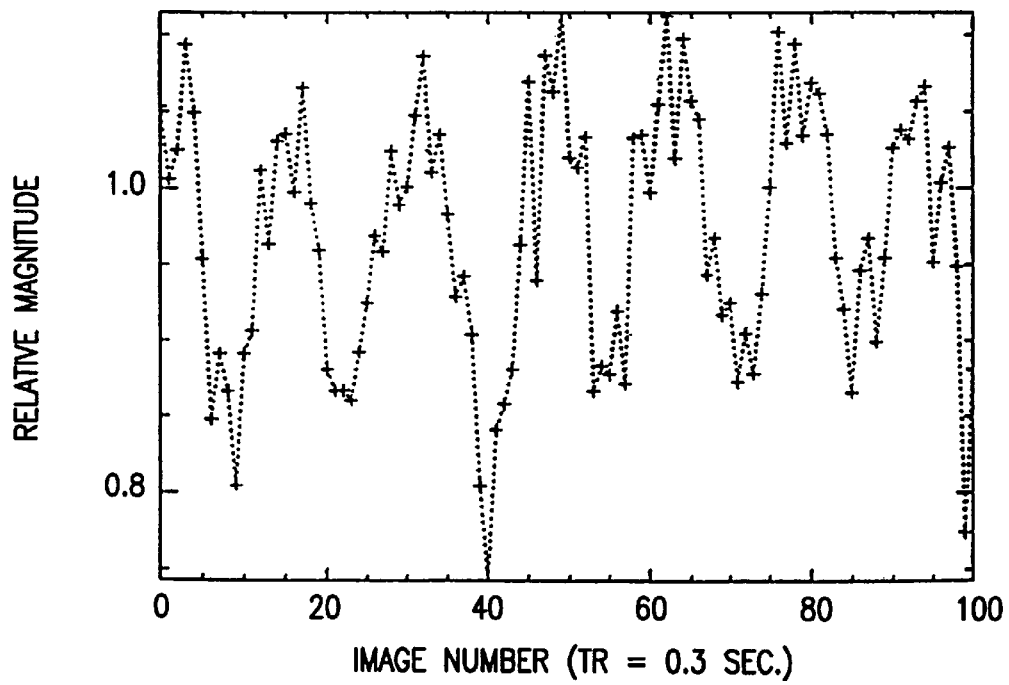
Figure 5A:
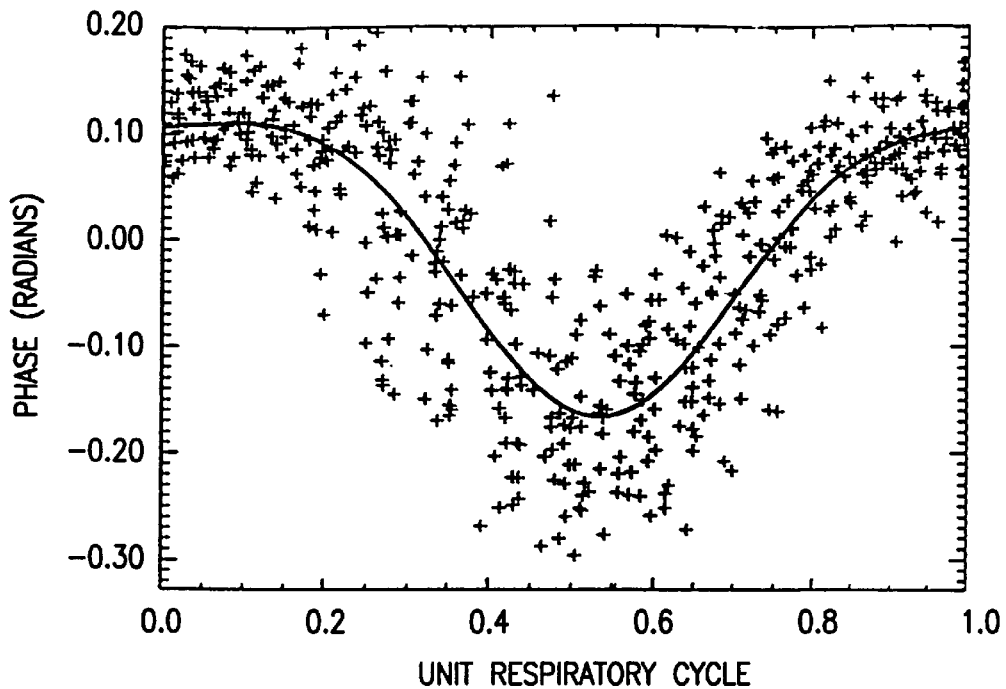
FIG. 5a shows the phase of the k-space data of FIG. 4a plotted against relative temporal location in the respiratory cycle derived from retrospective processing, including a solid curve obtained from nonlinear fitting of the plotted data.
Figure 5B:
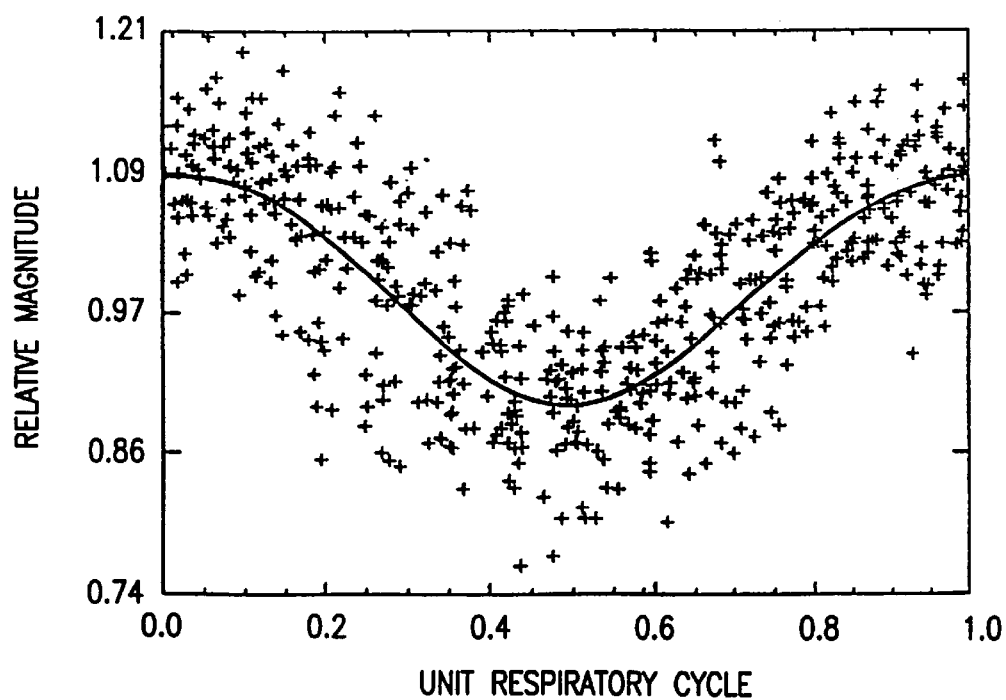
FIG. 5b shows the magnitude of the k-space data of FIG. 5a, including a solid curve obtained from nonlinear fitting of the plotted data.
Figure 6A:
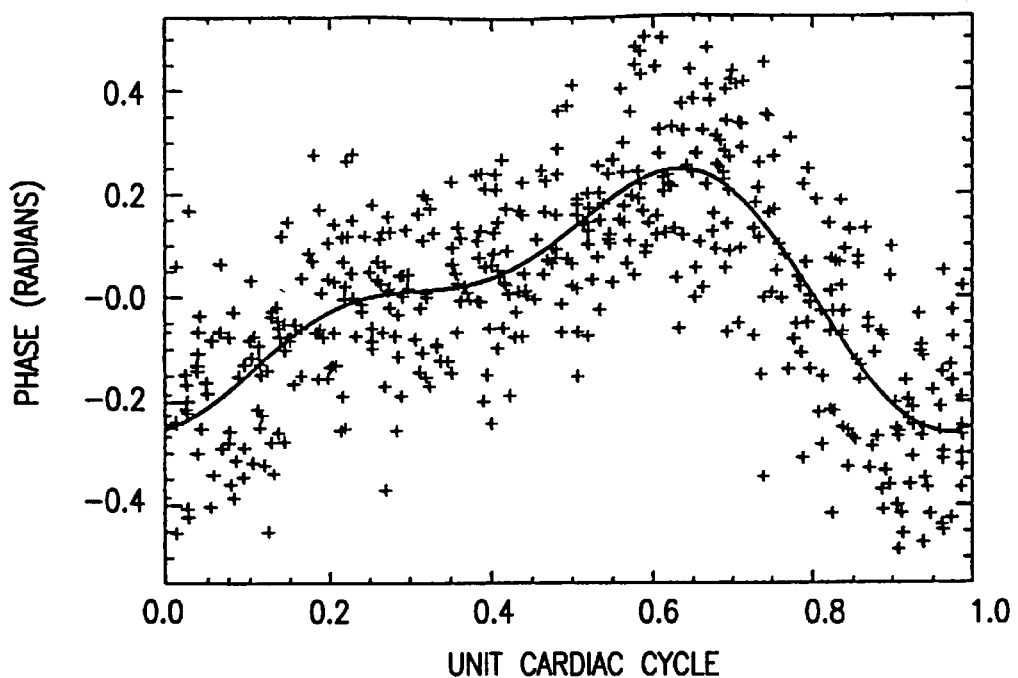
FIG. 6a shows the phase of a k-space data point with substantial cardiac variation plotted against their relative temporal location in the cardiac cycle, including a solid curve obtained from nonlinear fitting of the plotted data.
Figure 6B:
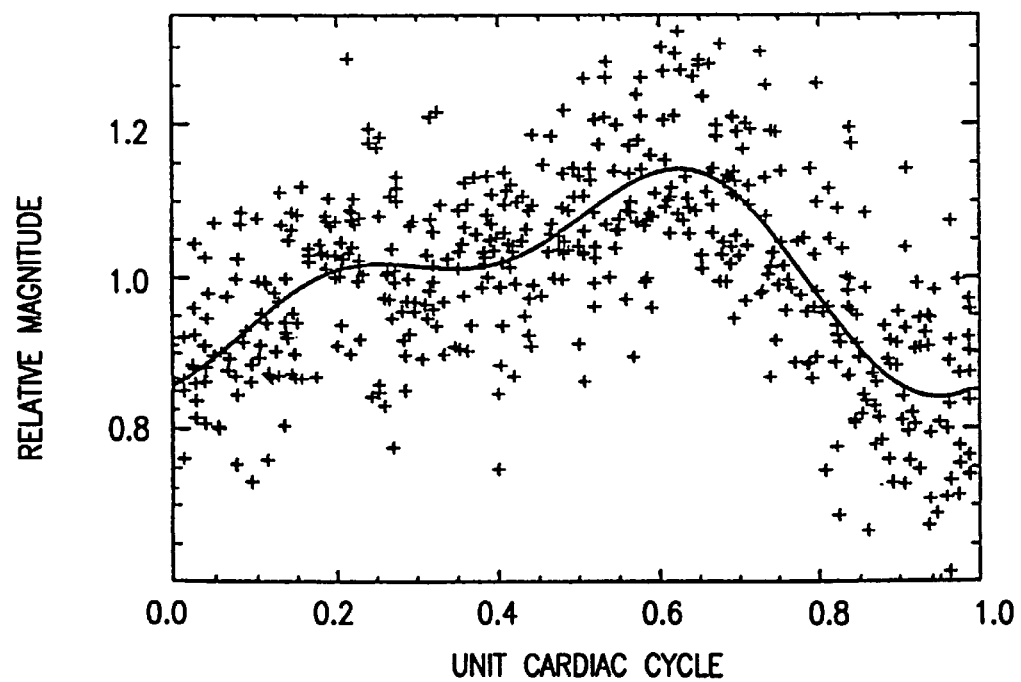
FIG. 6b shows the magnitude of the k-space data of FIG. 6a, including a solid curve obtained from nonlinear fitting of the plotted data.
Figure 7A:
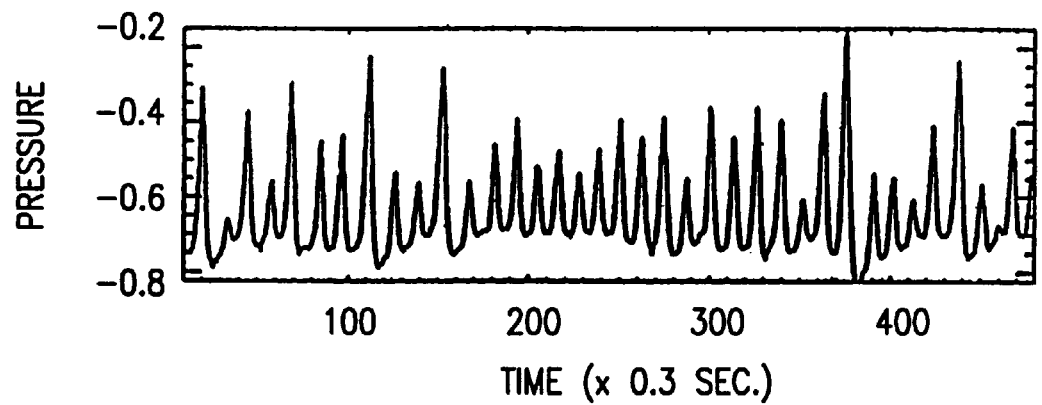
FIG. 7a shows the respiratory signal measured by a pressure belt of a patient who had substantial variation in respiration depth.
Figure 7B:
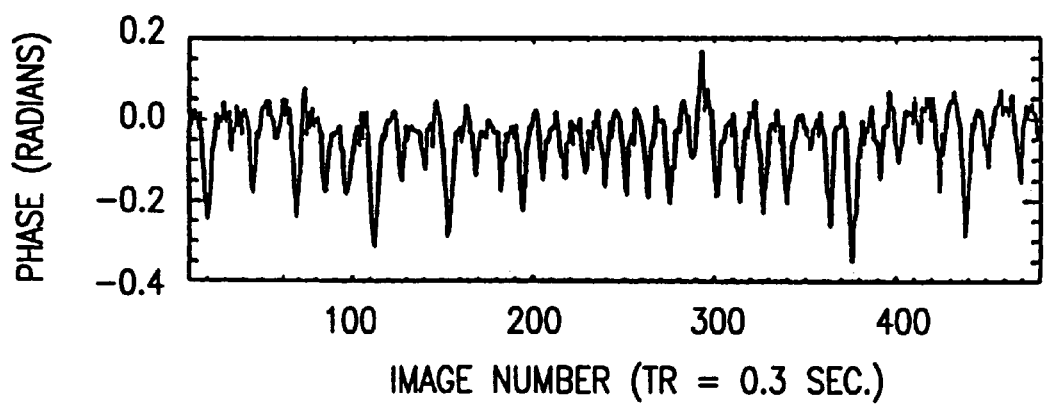
Figure 7C:
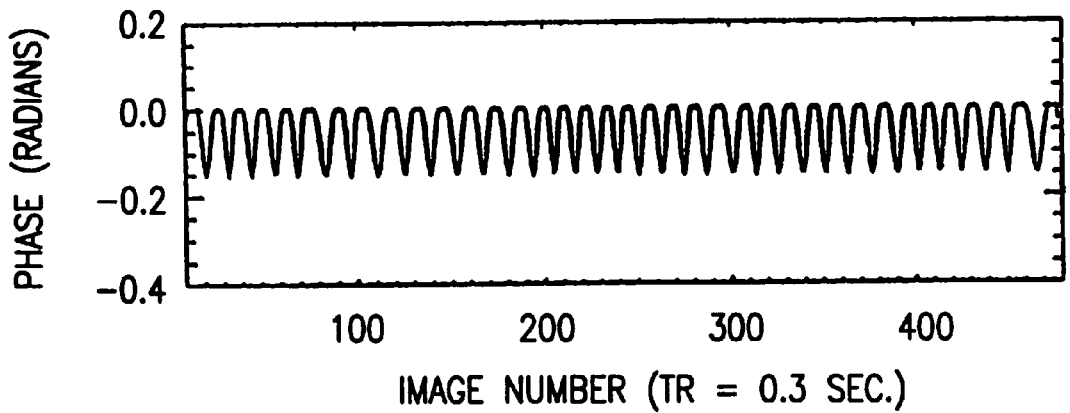
FIG. 7c shows the phase of the representative k-space point of FIG. 7b estimated without taking into account the variation in respiration depth.
Figure 7D:
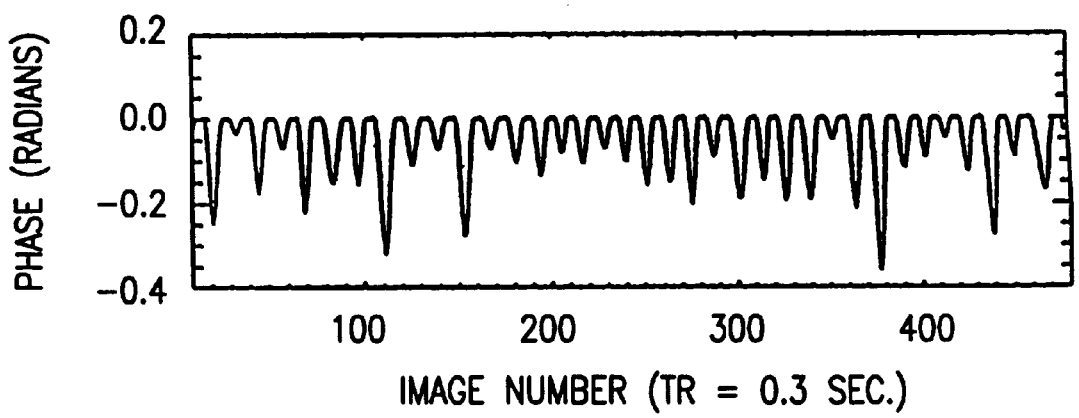
FIG. 7d shows the phase of the representative k-space point of FIG. 7c scaled by the respiration pressure in each cycle.

Retrospective fluctuation estimation was also applied to EPI. Five hundred EPI images were acquired with a TR of 0.3 s with no neuronal activation. One hundred samples of a representative k-space point are presented in FIGS. 4(a and b). With this TR, periodic fluctuations due to respiration or heart beat are visible. To correct for these fluctuations, a proper estimation of the physiological effects is needed. However, although the respiration and heart beat related changes are discernible, they can not be accurately estimated without reference to the physiological data due to the variation in the physiological periods, the noise in the data, activation related changes in stimulation studies, and possible interaction of the two types of effects. With retrospective synchronization, both cardiac and respiratory effects can be estimated. In FIGS. 5(a and b), the phase and the magnitude of the data shown in FIG. 4 are plotted in the unit respiration cycle and the nonlinear fits are shown as solid curves. For a k-space data point that exhibited substantial cardiac variation, the phase and the magnitude (after the removal of the respiratory effect) are plotted in FIG. 6 with the nonlinear fits shown as solid curves. Both figures demonstrate that a good estimation of the physiological effects can be obtained for EPI data as well.

The retrospectively estimated changes presented above characterize the average physiological effects; when scaled for the duration of an individual physiological cycle, they provide a good approximation of the variation in that cycle. However, in subjects with substantial variations in the depth of their respiration, temporally scaled unit cycle variation does not completely describe respiration related changes. In our studies, a correlation between the MR signal fluctuation and the measured pressure, which is a good approximation of the respiration depth, is found. Therefore, the pressure variation is used to augment the estimation of the signal variation in each respiration cycle. Results from a representative EPI study of a subject who had substantial variation in breathing are shown in FIGS. 7(a and b). The correlation between the phase of the measured signal and the respiration pressure is apparent. With only temporal scaling of the unit cycle phase variation, the predicted phase deviates from the actual phase substantially. In contrast, the phase predicted with scaling by the pressure within the corresponding cycle is in excellent agreement with the actual phase change. Clearly, this scaling provides an improved estimation.

Figure 8A:
FIG. 8a shows the anatomic image of a sagittal slice from a patient undergoing an echo-planar imaging (EPI) study without neuronal stimulation; the two boxes denoted 1 and 2 indicate the location of the central pixels whose time courses are presented in FIGS. 8d and 8e, respectively.
Figure 8B:
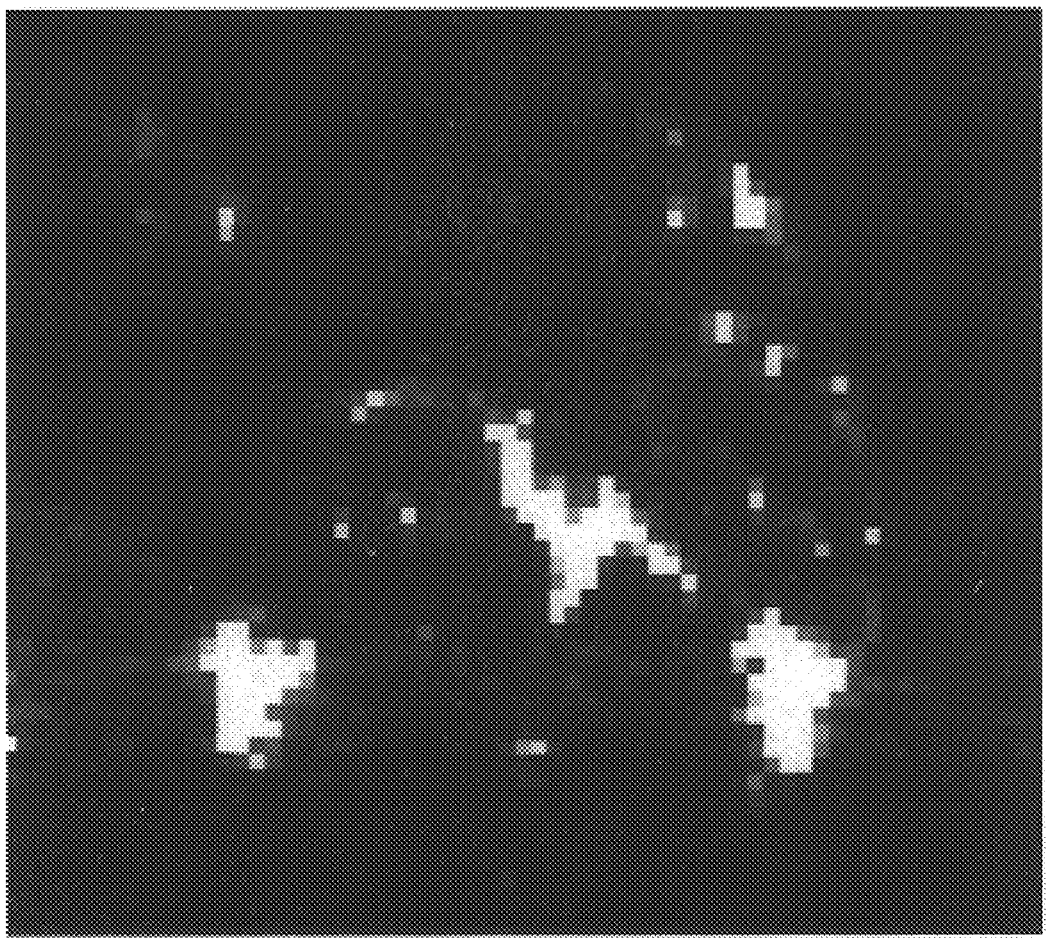
Figure 8C:
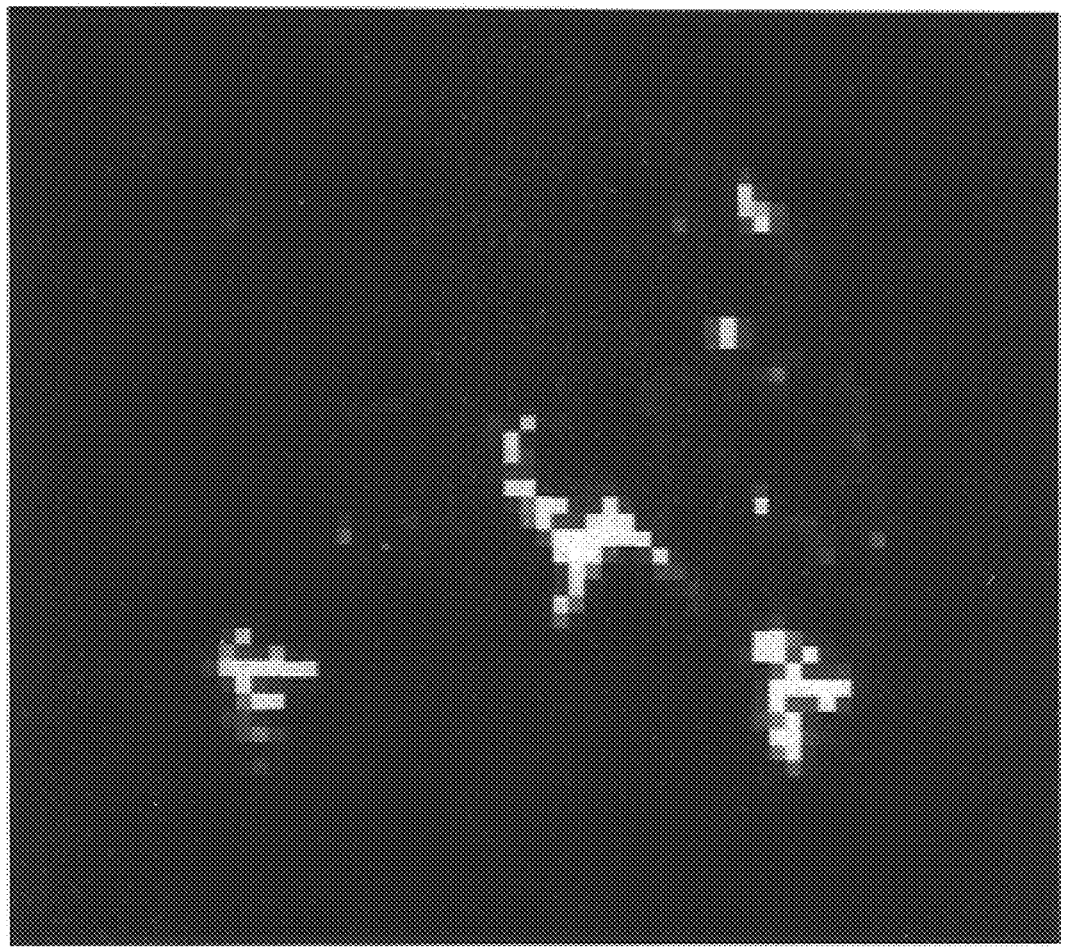
FIG. 8c shows a standard deviation map derived for the image of FIG. 8a corrected in accordance with the invention.
Figure 8D:
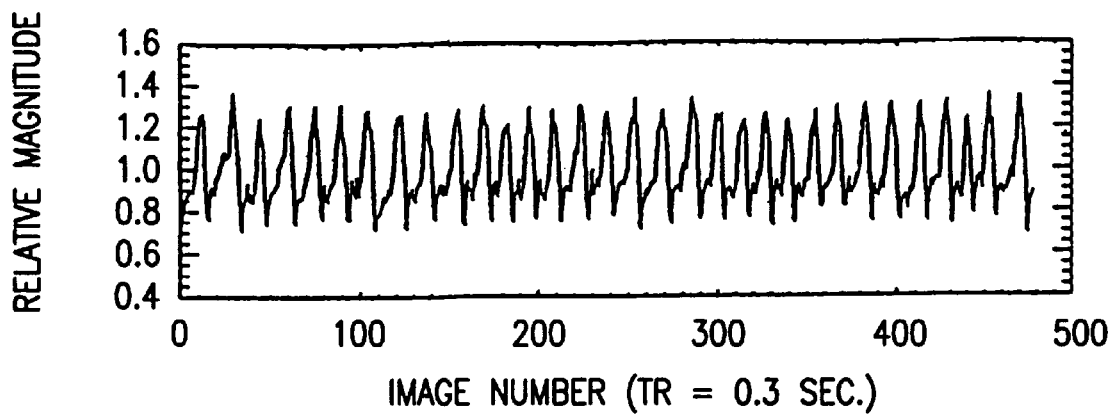
Figure 8D:
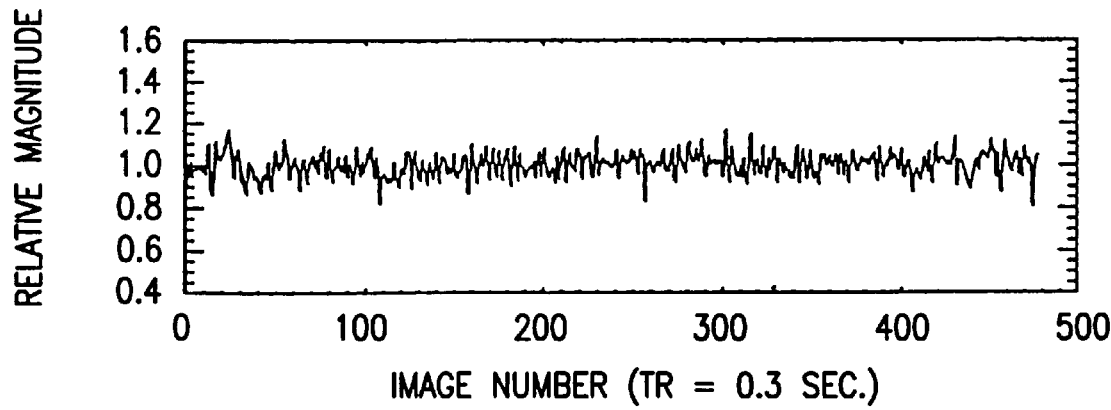
Figure 8E:
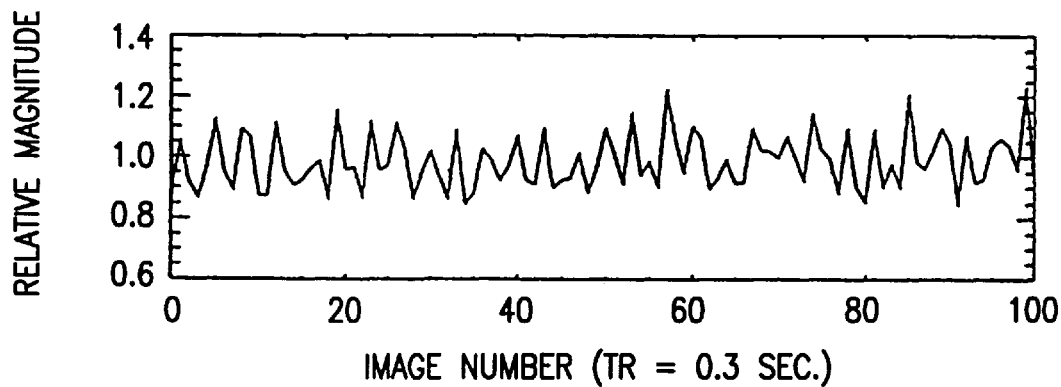
Figure 8E:
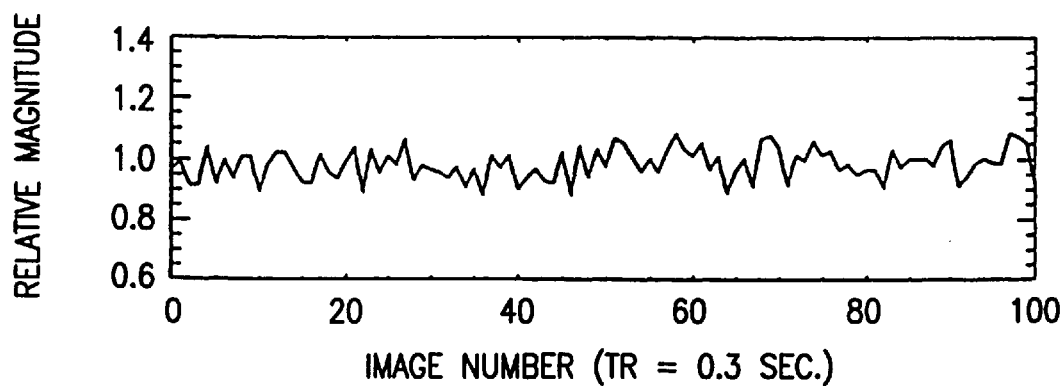
Figure 9A:
FIG. 9a shows the anatomic image of a sagittal slice from a FLASH study without neuronal stimulation, in which the cross indicates the pixel whose time courses are presented in FIG. 9d.
Figure 9B:
Figure 9C:
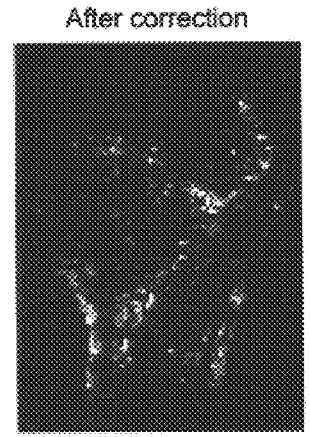
FIG. 9c shows a standard deviation map derived for an image corrected according the invention.
Figure 9D:
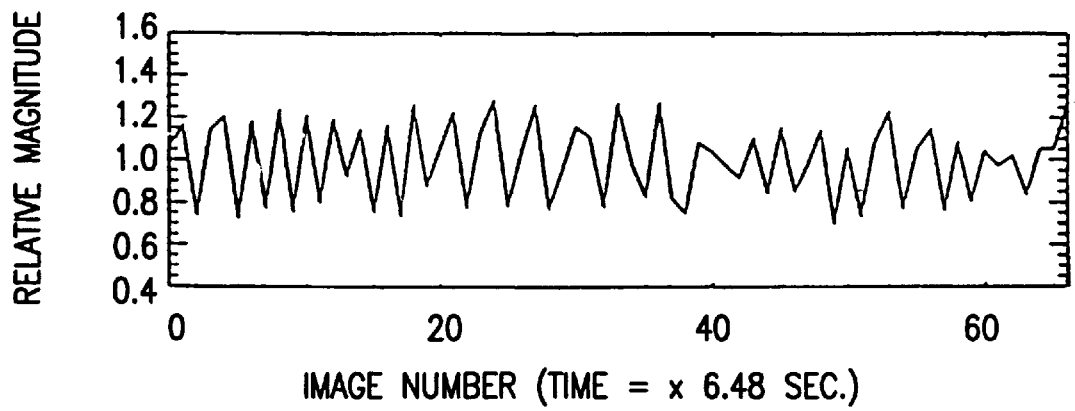
Figure 9D:
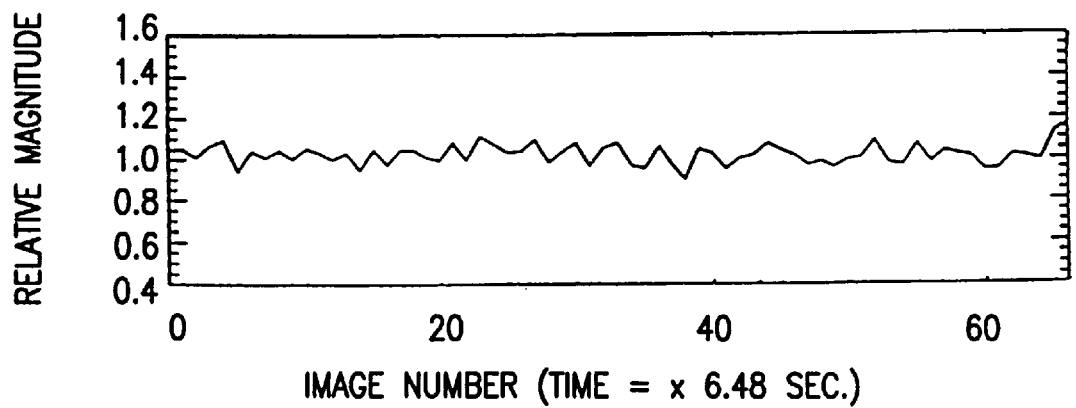

Motion correction using the inventive technique with both EPI and FLASH were performed. In the EPI study, a total of 500 images of a sagittal slice (FIG. 8a) were obtained without neuronal stimulation/task. For the correction of physiological fluctuations, the estimated variation was removed from each k-space data point. Standard deviation of each pixel was calculated to assess the fluctuations before and after the correction. FIGS. 8b and 8c illustrate the standard deviation maps before (FIG. 8b) and after (FIG. 8c) the correction of both respiration and cardiac pulsation related changes. It is evident that the standard deviations are substantially reduced in the corrected images, with the reduction ranging from 20%–60%. Time courses, with and without correction, in the two pixels indicated in FIG. 8a are presented in FIGS. 8d and 8e. Before the correction, pixel 1 exhibits substantial respiratory fluctuation, and pixel 2 is associated with significant cardiac fluctuation; these fluctuations are mostly removed upon the retrospective correction. Results from a representative FLASH study are shown in FIGS. 9(a, b, c and d). In this case, the standard deviation in the correction images is reduced by 20%–80%. Both studies indicated that the new correction technique is an effective approach.

Figure 10A:
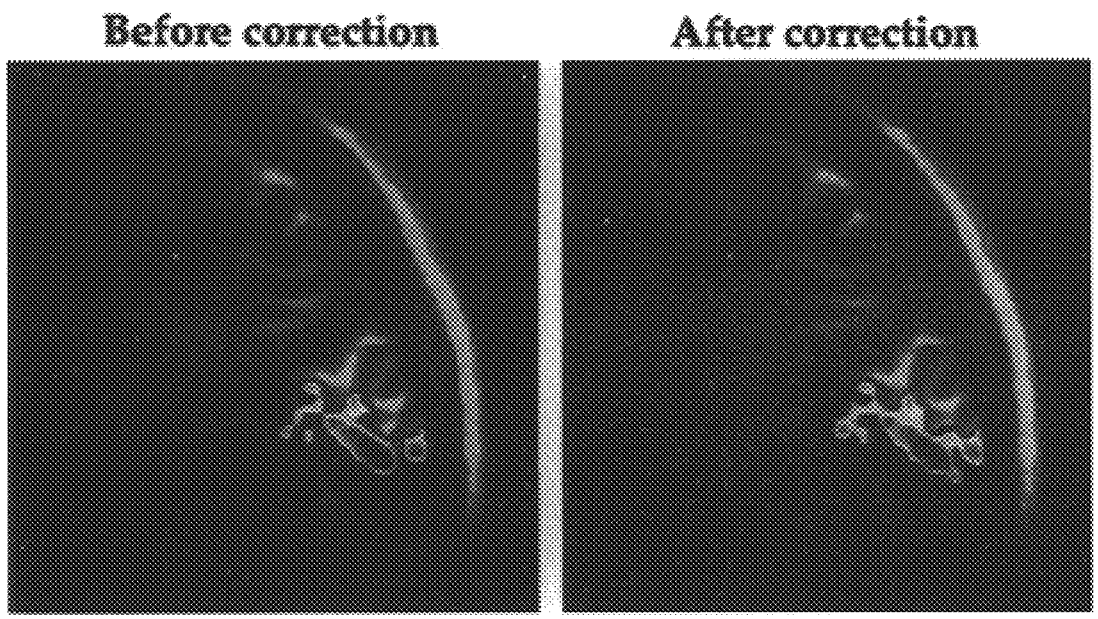
FIG. 10a shows a pair of photographs showing functional maps, obtained from images with and without correction, overlaid on the anatomic image of a visual stimulation study with EPI.
Figure 10B:
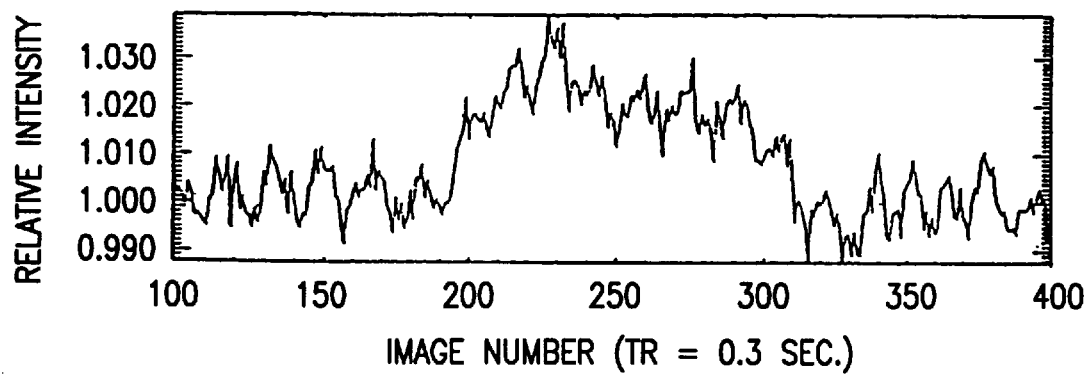
FIG. 10b shows the time courses, before and after correction, of an activated region of the study depicted in FIG. 10a, in which goggles were worn by the patient during images 180–280.
Figure 10B:
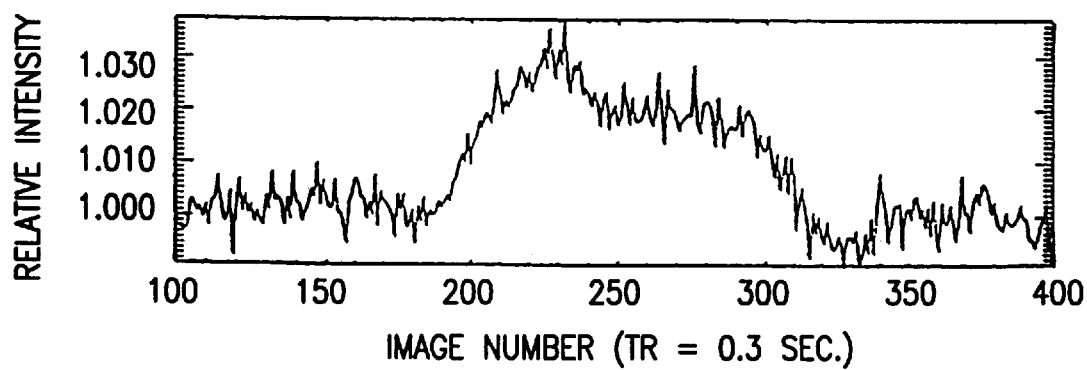
Figure 11A:
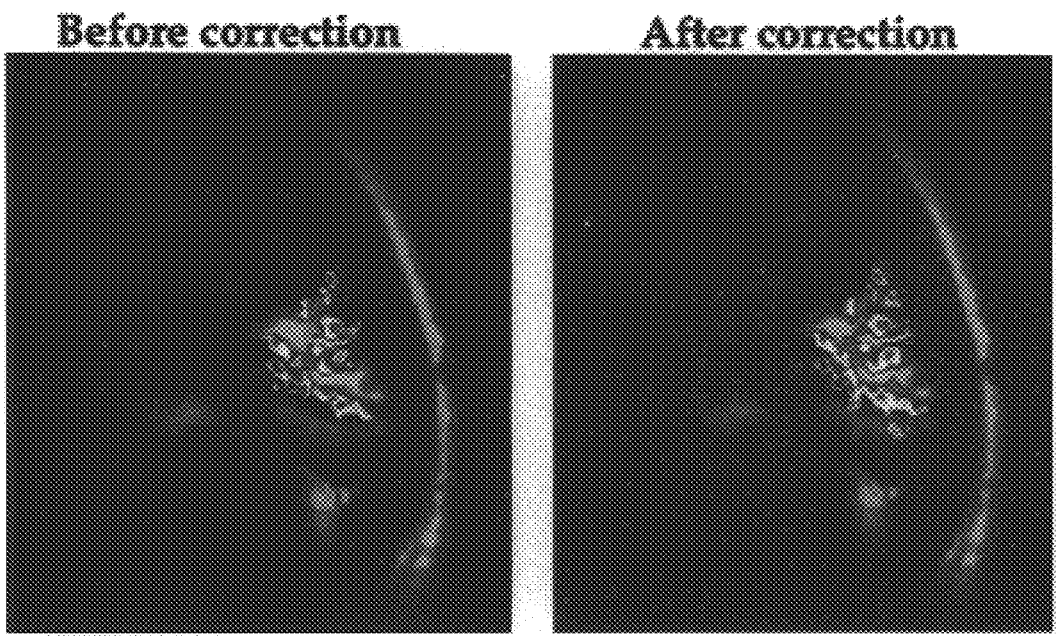
FIG. 11a shows a pair of photographs showing functional maps, obtained from images with and without correction, overlaid on the anatomic image of a visual stimulation study with FLASH.
Figure 11B:
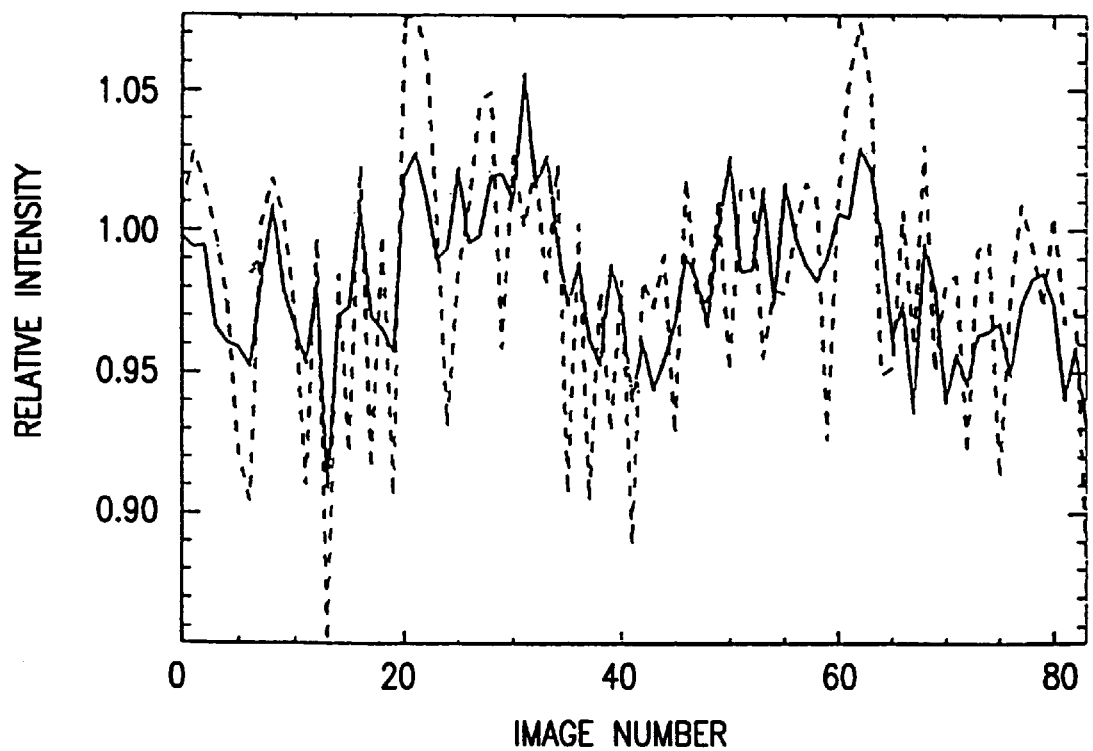
FIG. 11b shows the time courses, before (broken line) and after correction (solid line), of an activated region of the study depicted in FIG. 11a, in which goggles were worn by the patient during images 20–34 and 49–63.

Visual stimulation studies were obtained with both EPI and FLASH. Functional maps were derived by correlation with a box car function representing the stimulation paradigm and thresholded at a correlation threshold of 0.6. Maps derived from EPI images before and after the correction are shown in FIG. 10a. Time courses, before and after the correction, of an area with low level activation (2%) are presented in FIG. 10b. Results from the FLASH study are illustrated in FIG. 11. Both experiments demonstrate that physiological motion corrected data allowed better detection of low level activation. In the maps generated with EPI, the number of pixels activated with correction increases by 24% (38 vs. 47). The number of activated pixels in the maps derived from FLASH images increases by 33% (109 vs. 163). Comparison of time courses before and after the correction indicates that signal fluctuation due to physiologic motion has been reduced significantly while activation related changes were unaltered by the correction. As a result of the signal fluctuation reduction, activation induced signal variations can be more readily detected.

Reduction of fluctuation is observed in both EPI images and FLASH images. The improvement is spatially dependent. Specifically, more significant improvement is achieved in the CSF and at tissue boundaries. This observation can be explained by the fact that the pulsation of the brain induces more changes in these regions. It should also be noted that although the new technique is applicable to fMRI with all sequences, the improvement in FLASH was more dramatic since it requires relatively long acquisition times and is thus more susceptible to physiological motion.

Improvement of the sensitivity of fMRI may allow us to detect signal changes arising from small vessels, which correlate more closely with the spatial origin of neuronal activation. Recent studies have demonstrated that activation maps are dominated by large vessel contributions, particularly at low magnetic fields and at short echo times. Large vessel contributions are undesirable because they are expected to have poor correlation with the actual site of neuronal activity. Signal changes due to blood oxygenation level variation in small vessels have been observed but are very small. Ability to detect such small changes with the new technique will enable us to delineate the true spatial extent and location of the hemodynamic correlates to the neurobiological activity.

In addition to the reduction of fluctuation in image intensity, the temporal fluctuation in the phase of the complex image was also observed to be reduced. Although currently most of the fMRI studies are relying on detecting the magnitude change in the T2*-weighted images, this reduction in the phase fluctuation is potentially important for the study of activation induced phase changes previously reported. Such studies may be useful in addressing the mechanistic issues of fMRI, such as the vascular origin of the signal changes.

Unlike techniques for reducing motion artifacts in anatomic MRI, the correction technique of the invention removes temporal inconsistency between images. Inconsistencies within the k-space data of each image may be reduced to some extent and may still be present, leading to ghosting. Most importantly, the temporal dependence of the ghosts as a result of the physiological motion is eliminated. This reduction is demonstrated by the standard deviation maps shown in FIG. 8. On the other hand, the invention only considers the repeated motion of physiological origin and is not capable of correcting gross motion.

Figure 2A:
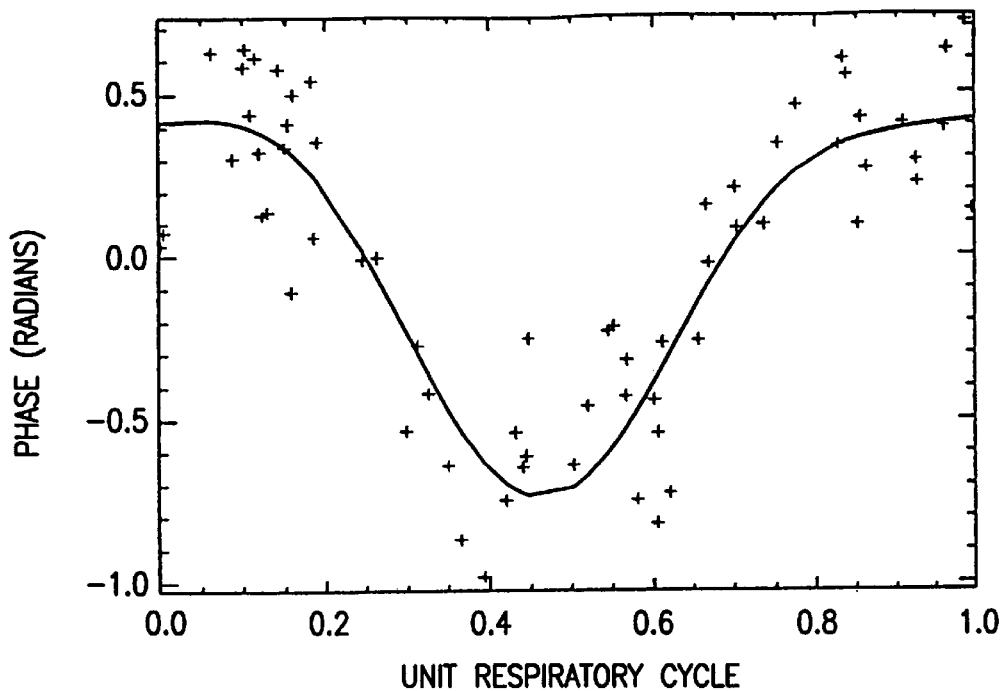
FIG. 2a shows the phase of the k-space data of FIG. 1a plotted against the respiratory cycle, including a solid curve obtained from nonlinear fitting of the plotted data.
Figure 2B:
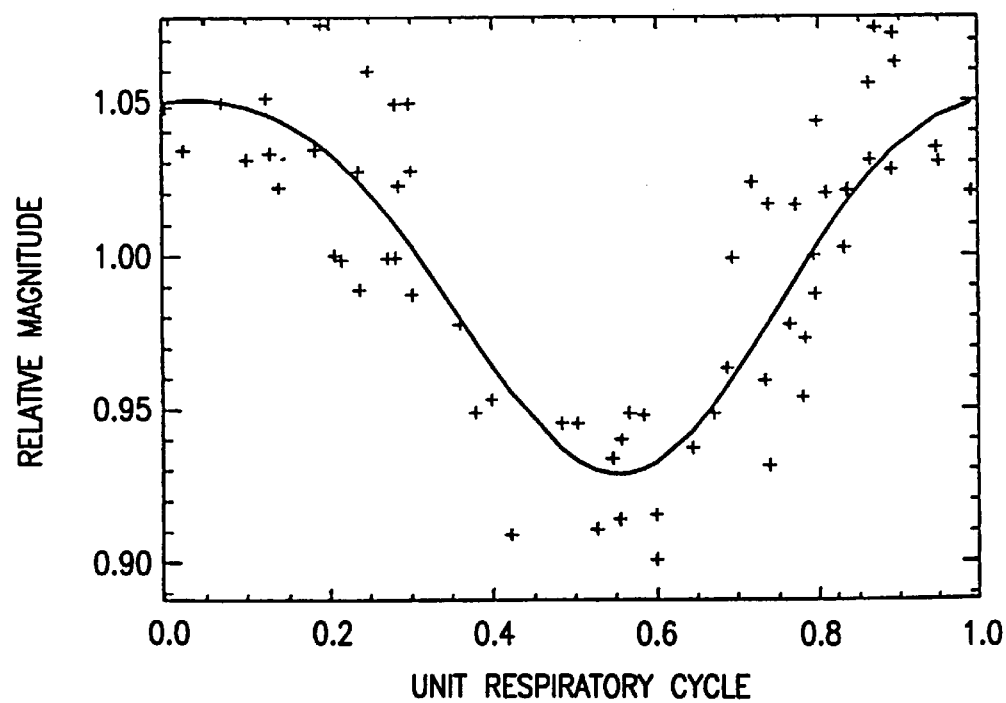
FIG. 2b shows the magnitude of the k-space data of FIG. 1b plotted against the respiratory cycle, including a solid curve obtained from nonlinear fitting of the plotted data.
Figure 3A:
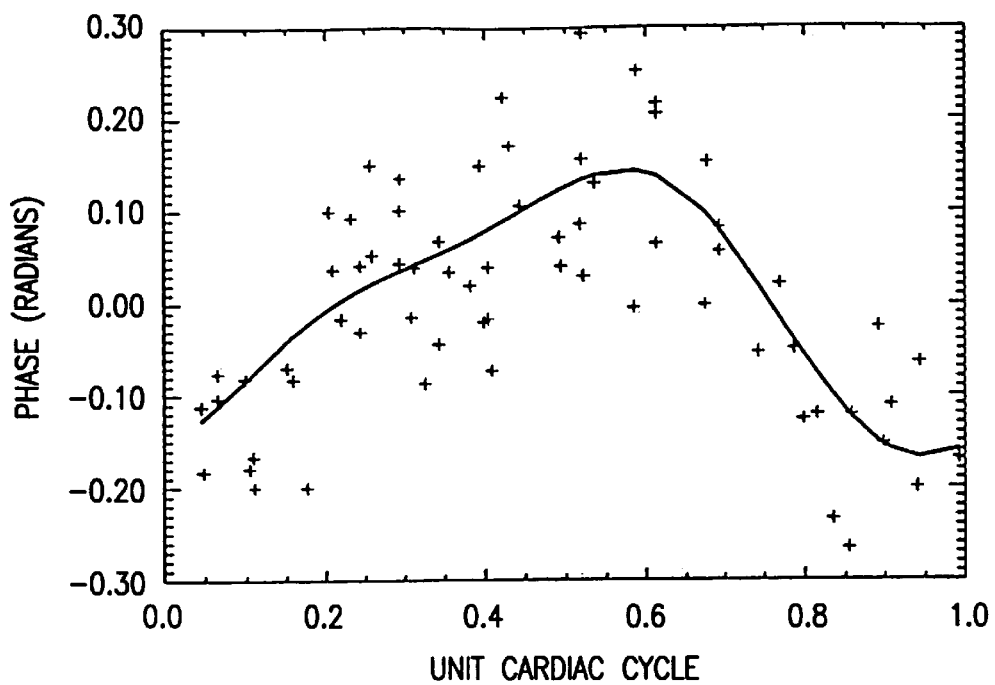
FIG. 3a shows the phase of a k-space data point with substantial cardiac variation plotted against their relative temporal location in the cardiac cycle, including a solid curve obtained from nonlinear fitting of the plotted data.
Figure 3B:
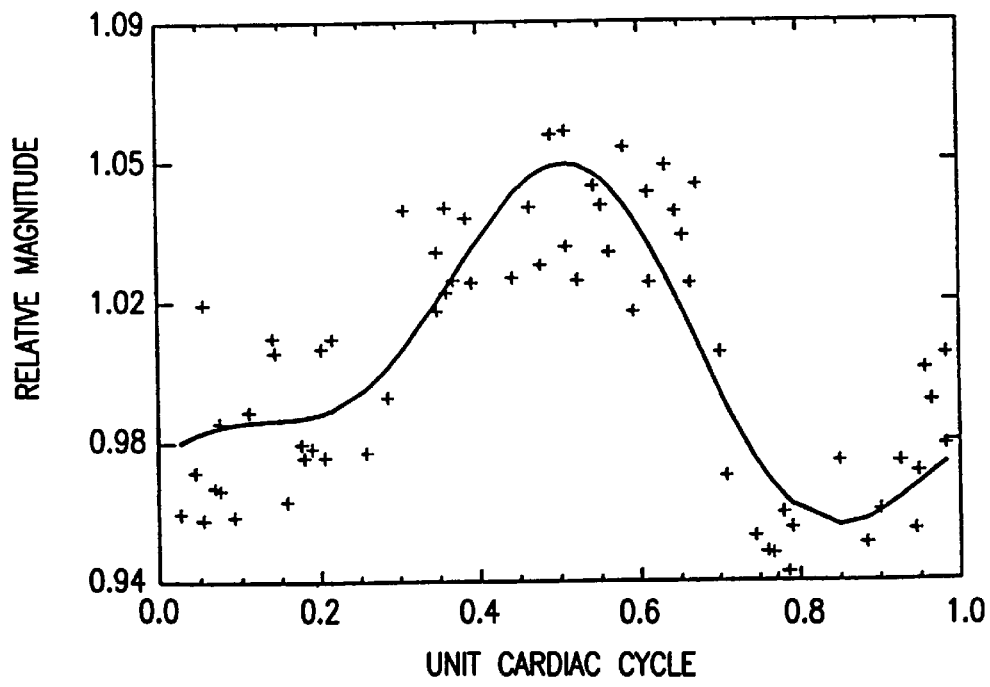
FIG. 3b shows the magnitude of the k-space data of FIG. 3a, including a solid curve obtained from nonlinear fitting of the plotted data.

The main assumption of this work is that the physiological effects are pseudoperiodic. This assumption is experimentally verified. As indicated in FIGS. 2 and 3($a$ and $b$), the measured signals exhibit a systematic physiological variation which depends largely on the relative position within individual physiological cycle, and it is possible to retrospectively estimate the physiological variation in a unit cycle for each k-space point if the number of images is sufficiently large despite that acquisition time per image is longer than the physiological period. Furthermore, in cases when the phase within the respiratory cycle alone is inadequate to determine the respiratory induced signal fluctuations due to the varying depth of a subject's respiration, it is possible to employ the measured pressure to augment the estimation of the variation within each individual breathing cycle.

When the number of images in a study is relatively large (e.g. >100), the unit cycle variation may be estimated by smoothing the measured data within the corresponding cycle. For example, a moving average with a window specified as a fraction of the unit cycle can be used, and the boundary condition can be imposed by periodic extension of the unit cycle data. Such an approach is independent of an assumed functional form and is more general.

In estimating physiological effects, we found that individual k-space points are affected differently. For instance, because the effect of respiration is approximately global, it is expected to affect all the points in the k-space; however, the effect depends on the particular location in the k-space and varies from experiment to experiment. Since the effect of cardiac pulsation is localized to regions within and surrounding the vessels and in regions affected by CSF, the points affected most are at high k-space locations. Due to the complexity of the physiological effects, there is little similarity between points of constant ky (phase-encoding). According to these observations, successful correction requires consideration of all points in the k-space. However, the presence of random noise may make it advantageous to consider k-space points which exhibit significant physiological variation relative to random noise. In most cases, such consideration is not necessary because random noise does not introduce significant error to the least squares fitting. In some studies, a test for the goodness of fit was performed to disregard k-space points with low SNR in the correction; however, we found that this step increased the computational time without an improvement in the final results.

In addition to the dependence on the location in k-space, respiration effects also depend on the location of the slice in the superior-inferior direction. The FLASH data shown in FIG. 1. exhibit more variation, partially due to that the sensitive region of the coil is more inferior (closer to the chest; see FIG. 9$a$). This observation is consistent with the susceptibility effect of the organs in the chest and abdomen.

In fMRI studies, the physiological effects may be correlated (in time) with the activation induced signal changes. In estimating the unit cycle variation, the effect of correlation is obviated by using the data acquired during the resting period alone. The implicit assumption of such an approach is that physiological motion effects are not strongly coupled to the neuronal activation. Experimentally, the correlation can be minimized by making the resting and stimulation periods much longer than the physiological periods. Under the condition of negligible correlation, the data acquired during both resting and stimulation periods can be used for the estimation of the physiological effects, and the activation induced changes lead to additional scattering of the data and possibly a DC component in the fits but do not alter the shape of the fits. Since the correction does not utilize the DC component, it is transparent to activation related signal changes. On the other hand, it is also possible to gauge the correlation effect by comparing two estimates of each unit cycle variation, one obtained based on the data acquired during resting period alone and the other based on all data obtained in the paradigm. In some of our studies (not presented here), both ways of estimation were used and results were compared. The difference between the two was found to be small, suggesting that the physiological effects are not strongly coupled to the activation and not substantially correlated with the activation in these particular studies. However, the correlation is in general present and the use of the baseline data alone in the estimation is likely more reliable.

The two variables, i.e., respiration phase and cardiac phase, are likely to be correlated. To account for this correlation, the respiratory effects are corrected first before the cardiac effects are estimated and removed. The order of the correction is chosen since the respiratory effects are expected to be more prominent. As a result, although the estimation of respiratory effects are not synchronize to a particular point of the cardiac cycle, the modeling is still valid. Furthermore, estimation of cardiac effects is not affected by respiration because the effect of respiration is removed first. If the two dependent variables are not correlated, the order of the correction is unimportant.

EXAMPLE II

All MRI experiments were conducted on a 4 T whole body system with a 1.25 m diameter bore (SISCo/Siemens)

and a quadrature surface coil. The magnet is equipped with a head gradient insert which produces a maximum gradient of 3 G/cm with a rise time of 180 µs in all three axes. To minimize gross motion, a head molding system was used to immobilize the subject. Inversion recovery T1-weighted images were acquired for identification of region of interest and anatomic reference. Consecutive T1*-weighted images were then collected for the slice that contains the identified region. For validation, the respiratory and cardiac activities of the subject are monitored during the acquisition of T2*-weighted images as previously described. Visual stimulation studies were performed in 9 subjects, with both FLASH (80–100 images with 128×128 matrix, slice thickness=5 mm, TR/TE=50/35 ms, FOV=20×20 cm$^2$, α=30 degrees) and EPI (400–500 images with TR/TE of 0.1 s/30 ms, matrix size=64×64, and an FOV=20×20 cm$^2$). Stimulation of the primary visual cortex was achieved with light emitting diode goggles (Grass Instruments) flashing at 8 to 16 Hz. A sagittal slice 0.6 cm away from the midline was studied. Each study consisted of repeated alternation between periods of light off and light on. The fMRI raw data were processed to remove the physiological motion. Functional activation maps were generated using a cross-correlation technique. Functional maps derived from the original images, the images corrected using the wireless technique, and those processed with the technique using external monitoring were compared.

Figure 12:
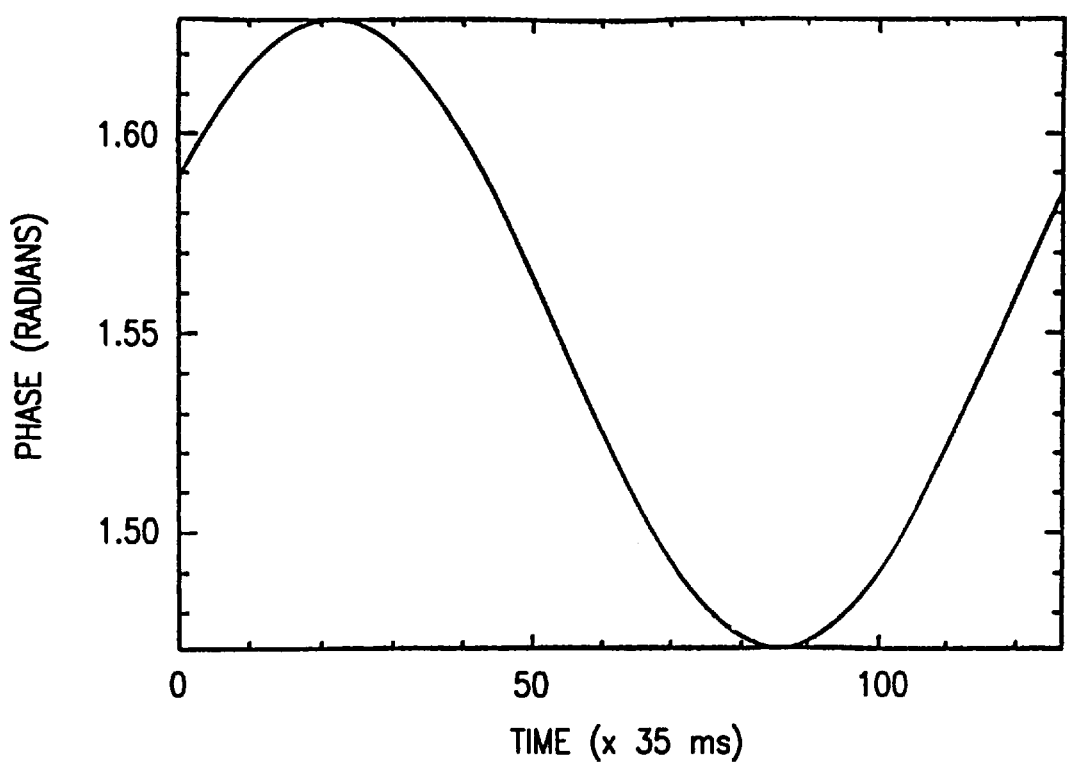
FIG. 12 shows the phase of the center of navigator echoes in a FLASH data set, processed with a low-pass digital filter with a cut-off frequency of 0.5 Hz.
Figure 13A:
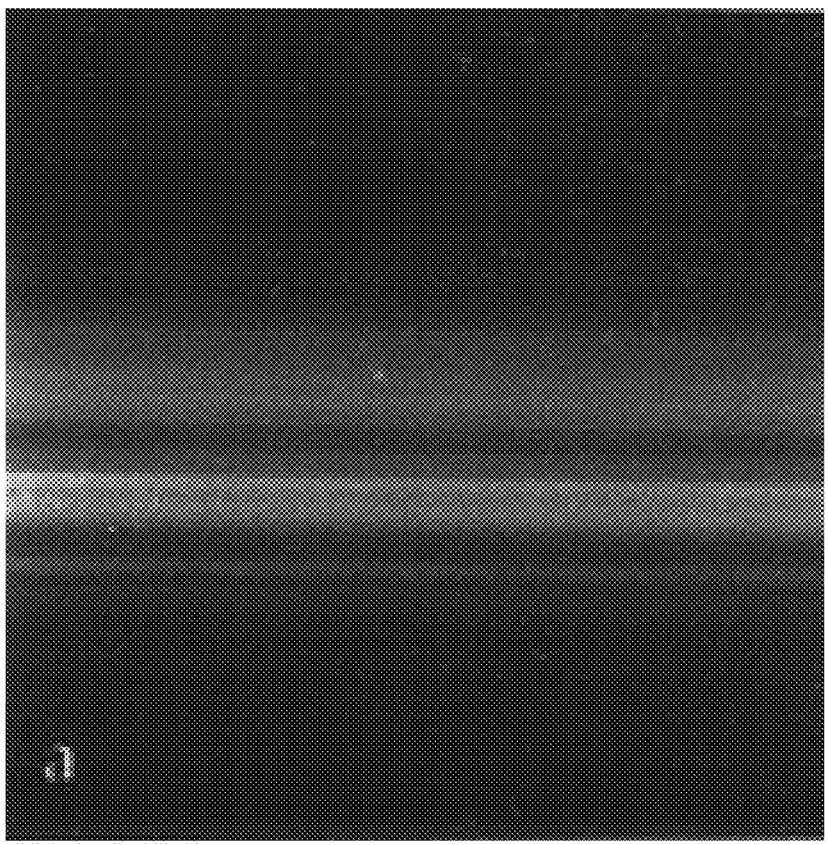
FIG. 13a shows projections obtained from navigator echoes in a FLASH data set, in which each column corresponds to a projection, and projections obtained at different time are arranged horizontally; the arrow points to the location along the projection identified by the search program as the representation of the cardiac pulse.
Figure 13B:
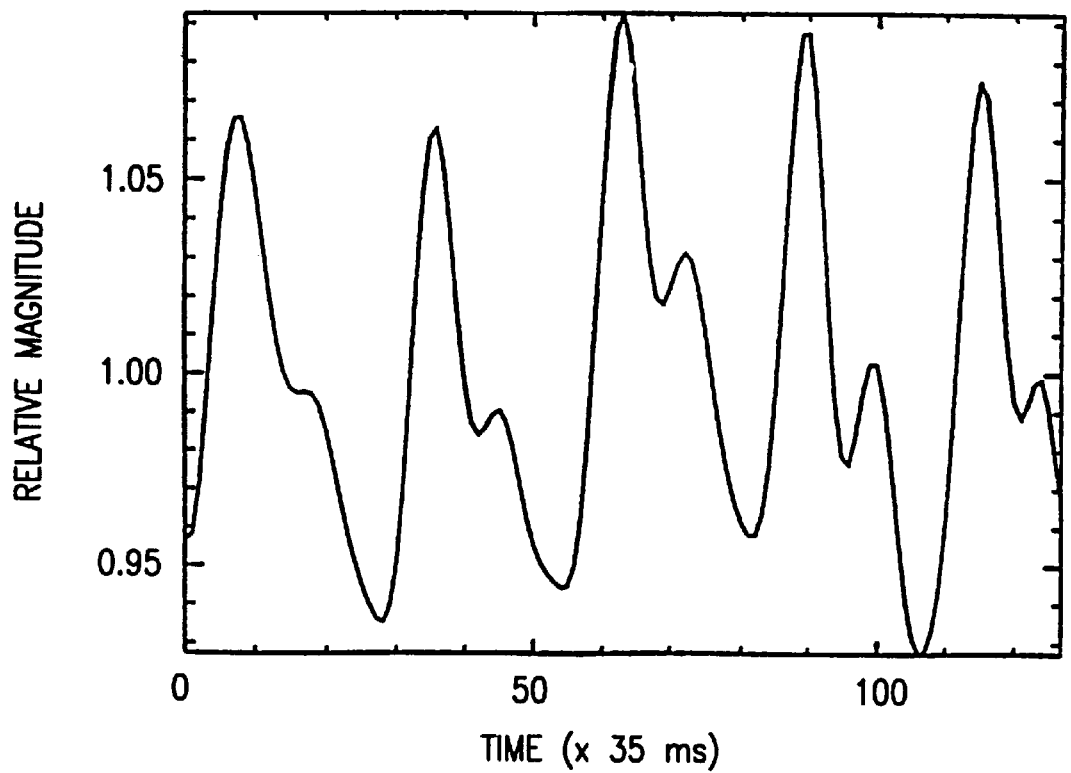

An example of the respiratory information obtained from the navigator echo in the FLASH image is shown in FIG. 12, in which respiratory modulation is evident. The phases of the center of the echo from all of the images are concatenated to provide the "effective respiratory pressure" which is subsequently utilized in the retrospective correction. The cardiac signal is obtained from the magnitude of the projection derived from the navigator echo. Projection data derived from echoes obtained during the acquisition of a FLASH image is shown in FIG. 13a, where the vertical axis represents the projection, and the horizontal axis corresponds to repetition. Because the cardiac effect is usually localized, it is necessary to search for regions along the projection where cardiac effect is prominent in order to detect the cardiac cycle. In this work, the cardiac profile is detected by using an automatic program that searches for the region that has the highest relative energy (spectral analysis) in the frequency range of 0.6 to 3.0 Hz, corresponding to heart rates of 36 to 180 beats per min. The temporal variation of the resultant region is taken as the "functional pulse" and used in the retrospective estimation and correction algorithm as in our previous technique. The arrow displayed in FIG. 13a indicates the region in the projection image identified by the search program. The "functional pulse" extracted from the image is illustrated in FIG. 13b.

Figure 14:
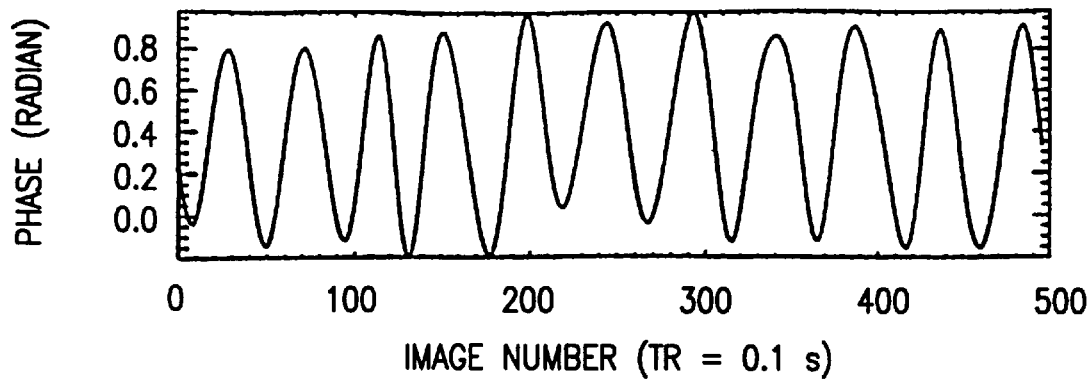
FIG. 14 shows the abdominal motion (bottom) and the phase (top) of the center k-space point of an EPI fMRI data set.
Figure 14:
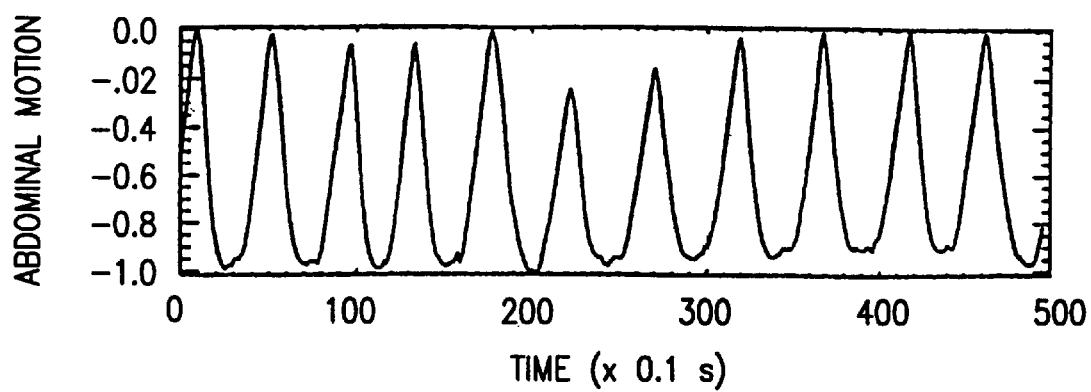

The phase variation of a representative center k-space point and the corresponding abdominal pressure are shown in FIG. 14. This figure illustrates that there is a high correlation between respiration and the phase of the center k-space; therefore, the phase provides an accurate representation of the respiratory behavior. To detect cardiac cycle, projections along both the phase-encoding and readout directions are used. Since the sampling window for each EPI image is very short (~30 ms), the projection along the phase-encoding direction is considered as acquired instantaneously. Furthermore, it is possible to obtain consecutive images fast enough for the detection of both cardiac and respiratory variations.

Figure 15A:
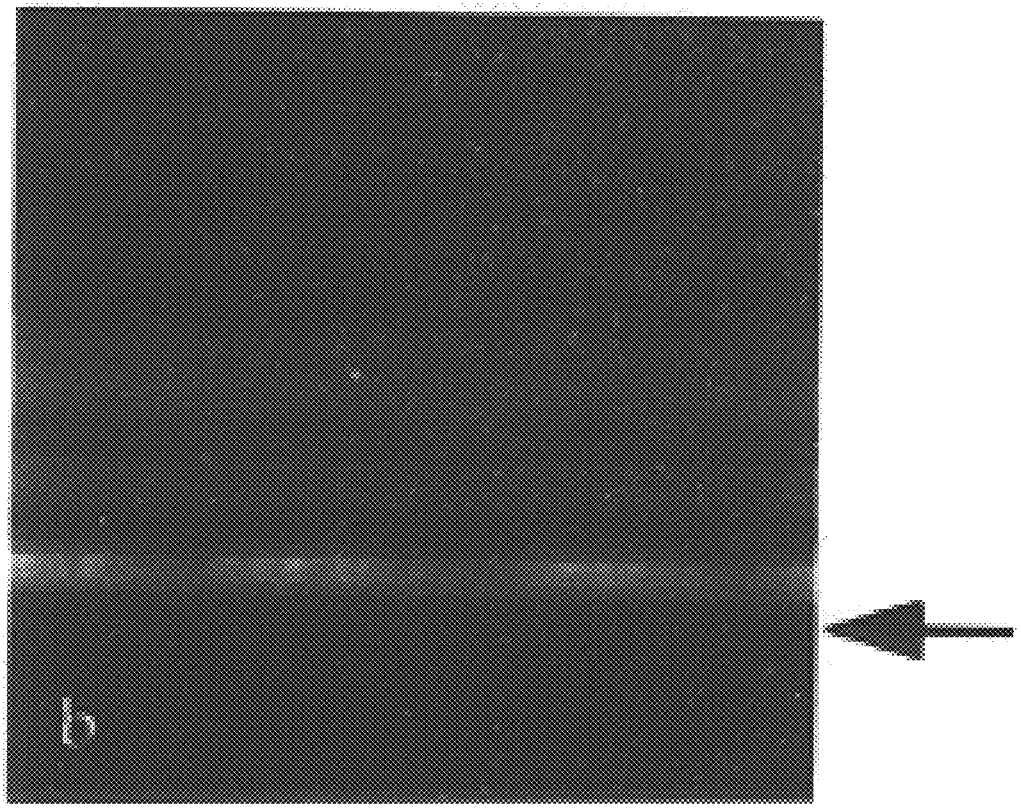
FIG. 15a shows the readout projections obtained from an EPI data set, displayed vertically with the horizontal direction representing time; the arrow marks the location identified by the automatic search program.
Figure 15B:
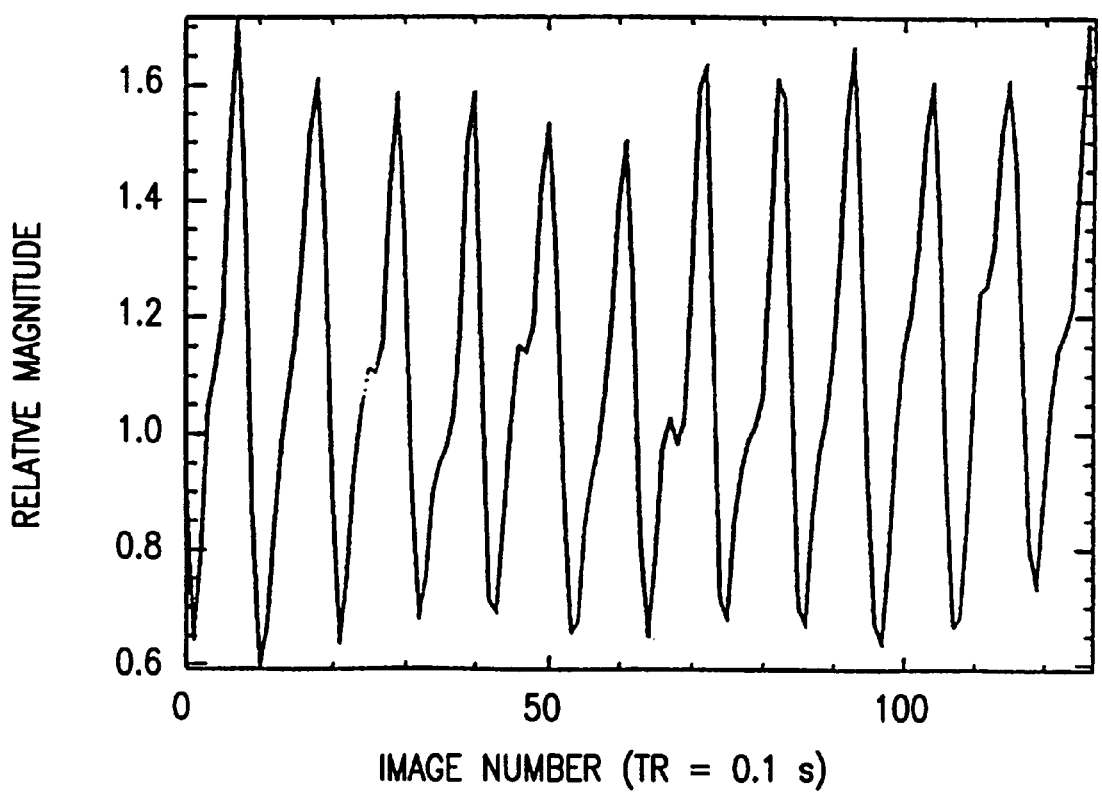
FIG. 15b shows the cardiac pulsation profile obtained from the projection data shown in FIG. 15a, from which high and low frequency oscillations unrelated to cardiac pulsation have been removed by a digital band-pass filter.

The projection image along the readout direction of the EPI data set is shown in FIG. 15a. The cardiac timing extracted by searching through the projection data as described above is shown FIG. 15b, where the cardiac variation is readily detected.

Figure 16:
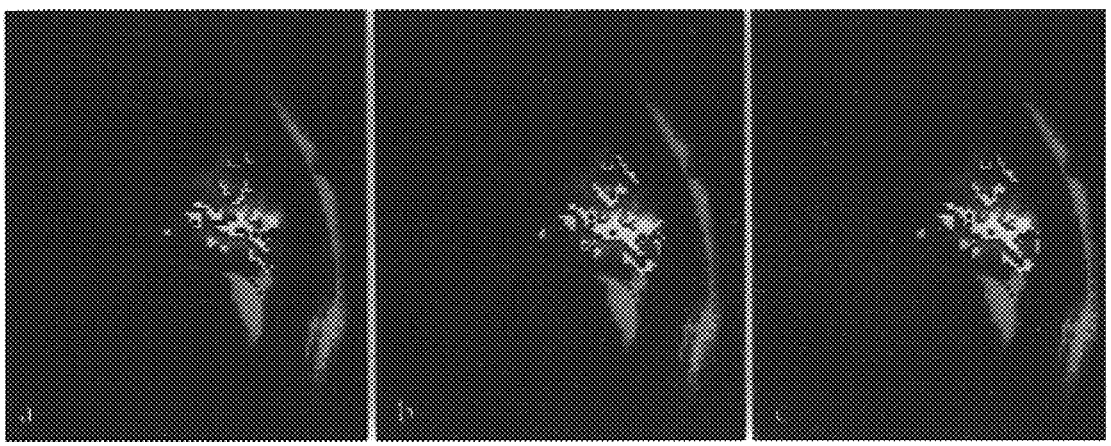
FIG. 16a shows functional activation map of a visual FLASH study before correcting for cardiac and respiratory motion artifacts.
FIG. 16b shows the functional activation map derived from the FLASH data of FIG. 16a after retrospective correction based on external physiological monitoring.
FIG. 16c shows the functional activation map calculated from the FLASH data of FIG. 16a after processing according to the invention.
Figure 17A:
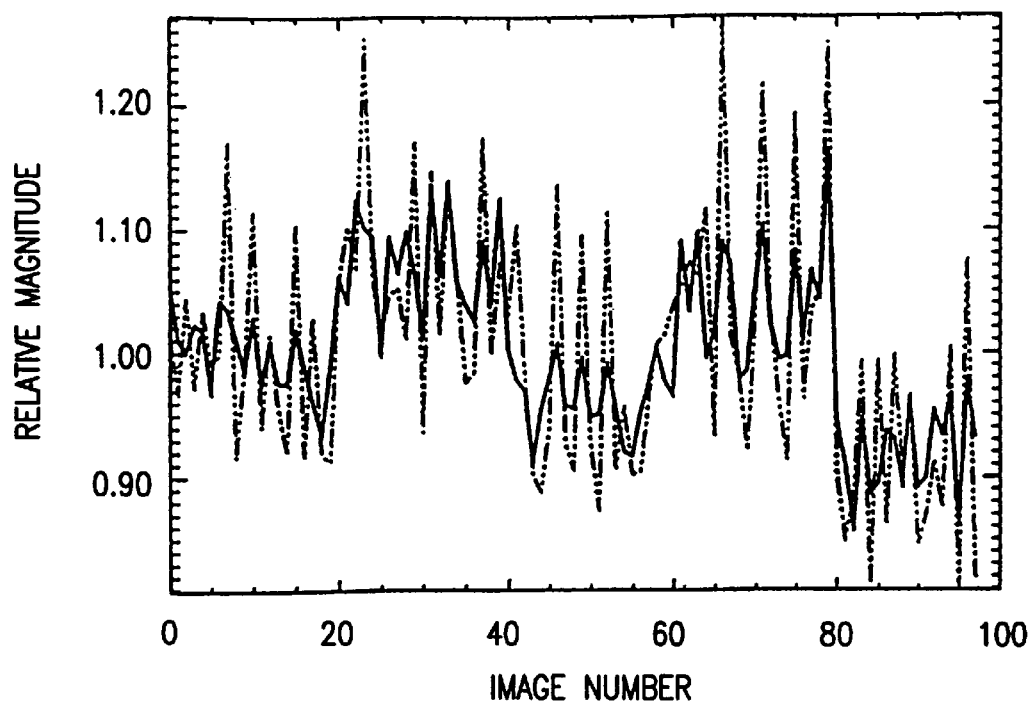
FIG. 17a shows the time course of a single voxel in a FLASH fMRI data set that is severely affected by physiology related motion, with the broken line indicating the time course of the original data before retrospective correction in accordance with the invention and the solid line indicating the time course of the same voxel after correction using the retrospective technique of the invention with external monitoring of physiology.
Figure 17B:
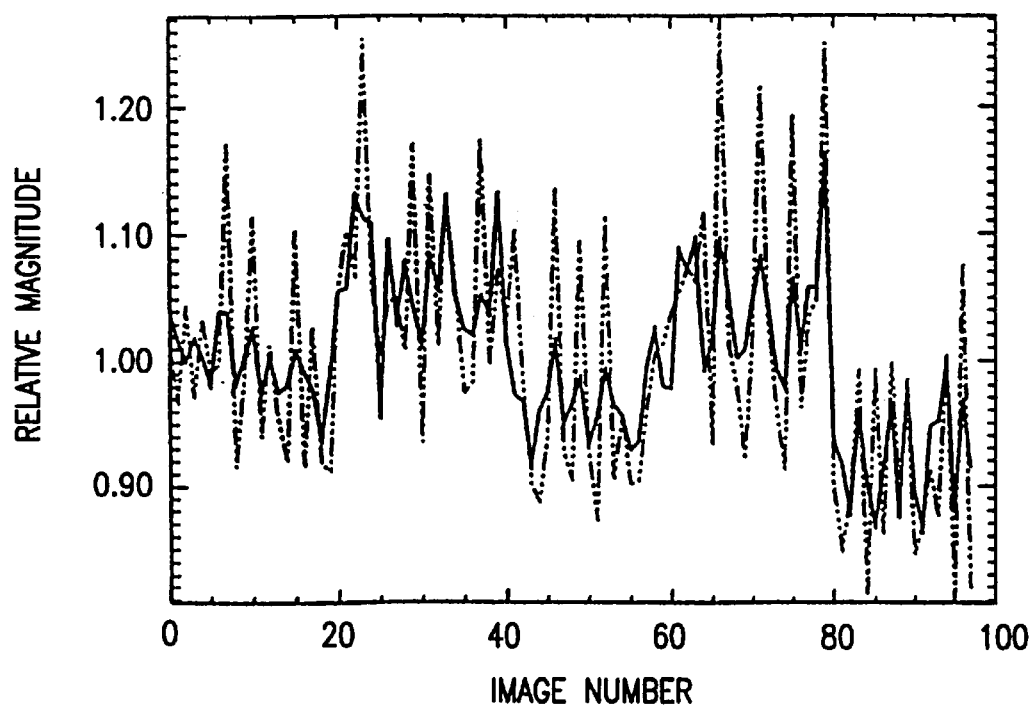
FIG. 17b shows the time course of the same voxel as in FIG. 17a except that the solid line represents the result of correction according to the invention but not based on external monitoring of physiology; the patient wore LED goggles during the acquisition of images 19–39 and 59–79.

Functional activation maps generated from a representative FLASH visual study are shown in FIGS. 16a, 16b and 16c. For comparison, outcomes from application of the external monitoring technique are also illustrated. In this particular study, 100 sagittal images were obtained with visual stimulation occurring during the acquisition of images 19–39 and 59–79. FIG. 16a illustrates the functional activation map derived from images without correcting for physiological artifacts, and FIGS. 16b and 16c show the corresponding functional activation maps after correcting for physiological effects using, respectively, the retrospective method with external monitoring (FIG. 16b) and the preferred technique (FIG. 16c). Functional maps were derived by correlating the fMRI data with a box car function representing the stimulation paradigm at a correlation threshold of 0.5. By calculating the number of "activated" pixels in the visual cortex, an improvement of approximately 30 40% was noted in all FLASH visual stimulation experiments when retrospective correction is utilized (for the study shown in FIGS. 16a–c, the number of "activated" pixels detected increases by 34%). Time courses, with and without correction, of a single voxel with substantial fluctuation are shown in FIGS. 17a and 17b, respectively. Comparison of these time courses reveals that signal fluctuation has been reduced significantly. These results demonstrate that the new technique reduces signal fluctuation and improves the functional activation maps in a similar fashion as the retrospective technique previously described.

Figure 18:
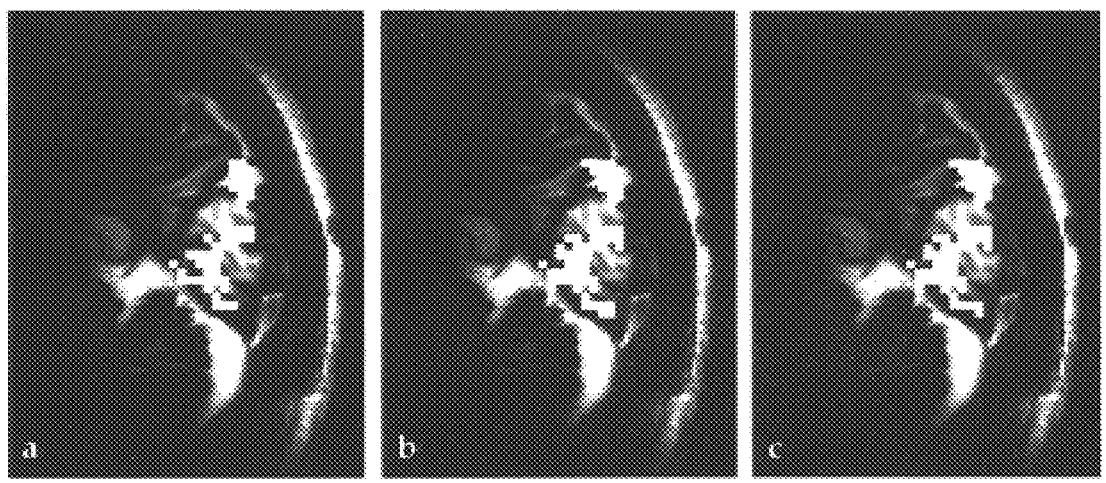
FIG. 18a shows the functional activation map of a visual study using an EPI sequence before correcting for cardiac and respiratory motion artifacts.
FIG. 18b shows the functional activation map derived from the EPI data of FIG. 18a after retrospective correction based on external physiological monitoring.
FIG. 18c shows the functional activation map calculated from the EPI data of FIG. 18a after processing according to the invention.
Figure 19A:
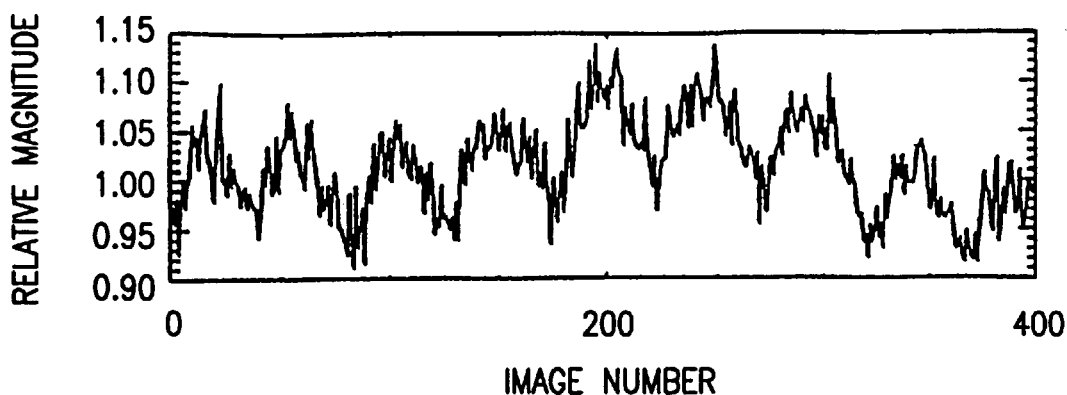
FIG. 19a shows the time course of a single voxel that exhibits substantial respiration-related signal variation, before retrospective correction.
Figure 19B:
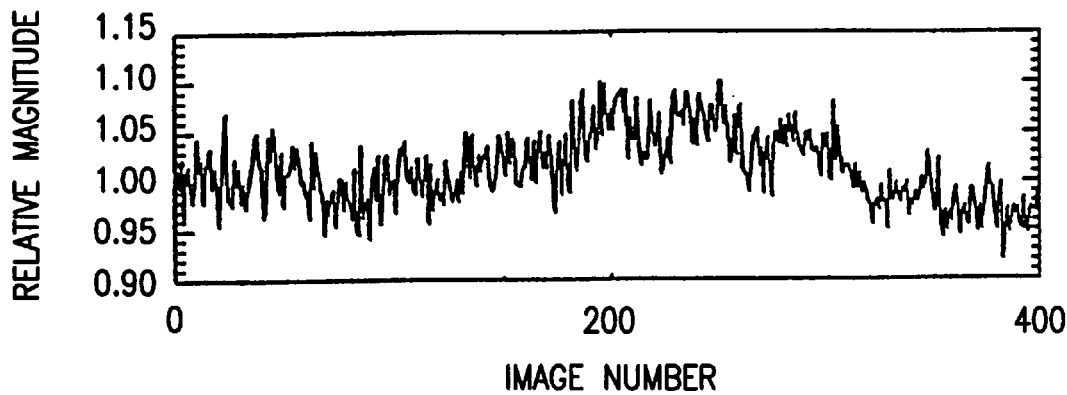
FIG. 19b shows the time course of the voxel of FIG. 19a after retrospective correction with external physiological monitoring.
Figure 19C:
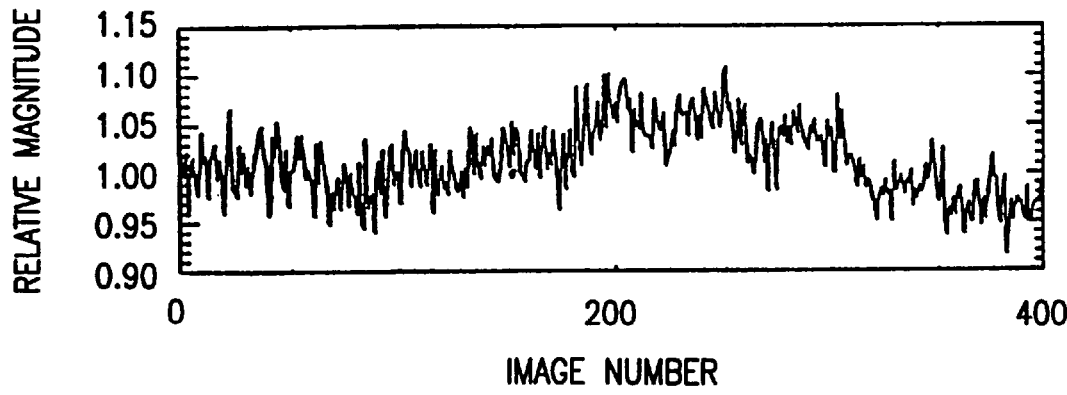
FIG. 19c shows the time course of the voxel of FIGS. 19a and 19b after being processed in accordance with the invention; the patient wore LED goggles during acquisition of images 100–250.
Figure 20A:
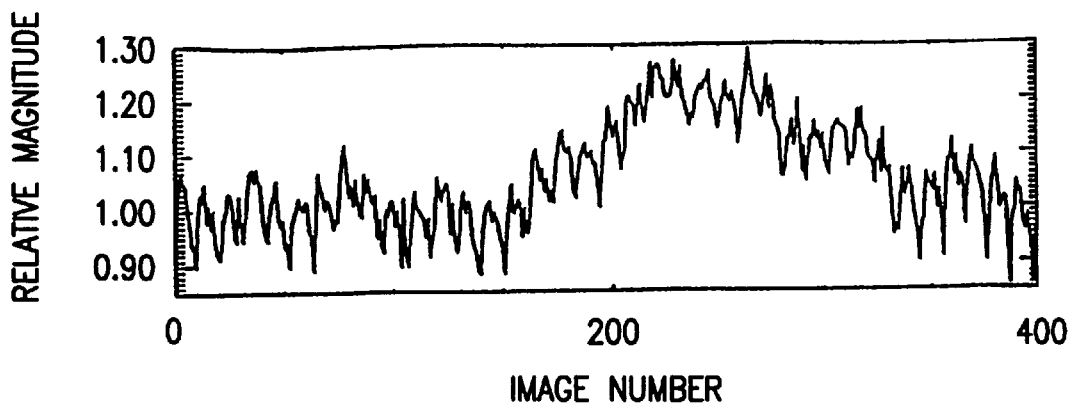
FIG. 20a shows the time course of a single voxel that exhibits substantial cardiac variation, before retrospective correction
Figure 20B:
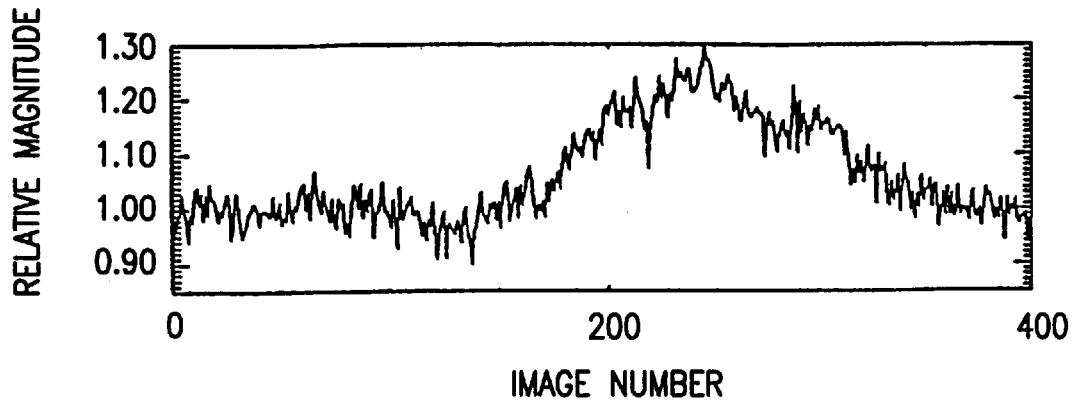
FIG. 20b shows the time course of the voxel of FIG. 20a after retrospective correction with external physiological monitoring.
Figure 20C:
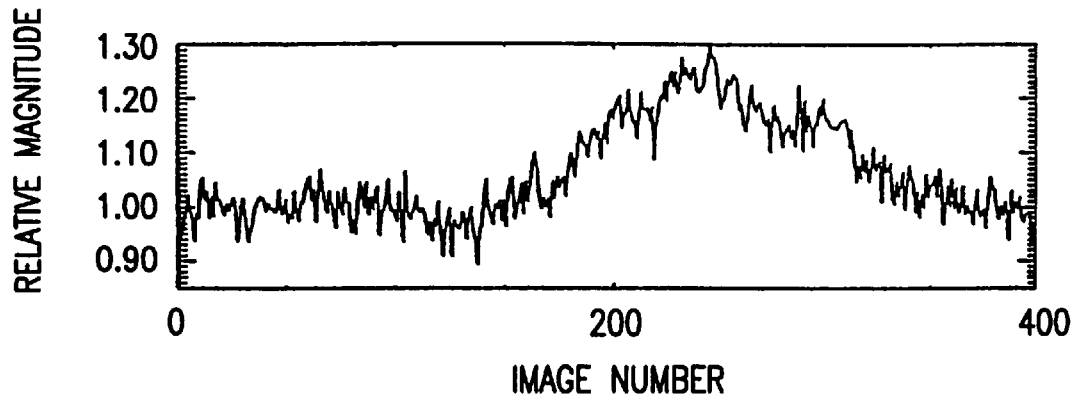
FIG. 20c shows the time course of the voxel of FIGS. 20a and 20b after being processed in accordance with the invention; the patient wore LED goggles during acquisition of images 100–250.

Functional activation maps derived from a representative EPI experiment are shown in FIGS. 18a, 18b and 18c. Four hundred echo planar images with a TR of 0.1 s were acquired with visual stimulation occurring during acquisition of images 100–250. Maps were generated from the original data (FIG. 18a), and data after correction by the retrospective technique with external monitoring (FIG. 18b), and by the preferred method (FIG. 18c). A cross-correlation method at a threshold of 0.6 was used. For this particular study, the number of activated pixels in images derived from both correction schemes increases by 26%, and the spatial extents of activation maps are almost identical in both cases (approximately 20–30% improvement was observed in all of the EPI studies). By carefully examining the signal variation in those regions that are identified as "activated" in the functional maps from the corrected data but not in the maps from the original data, we notice that these regions are severely affected by cardiac pulsation and respiration. The effect of respiration is most prominent in gray matter located at the edges (boundaries between CSF and brain tissue and between gray and white matters), and the effect of cardiac pulsation is most prominent in regions surrounding large vessels. Signal fluctuation due to these effects increases the standard deviation of the temporal fMRI series, leading to a decrease in the sensitivity of statistically detecting signal change related to neuronal activation. As a result, removal of physiological motion not only increases the spatial extent of the functional activation in regions surrounding vessels but also in gray matter located distant from the large vessels. Time courses of a single voxel with substantial respiratory and of a single voxel with substantial cardiac variations are shown in FIGS. 19 and 20, respectively.

Compared to the technique of Example I, i.e., the use of external monitoring, the preferred embodiment of the invention must acquire data sufficiently fast to capture the physiological motion. This is accomplished in single slice imaging by making the repetition time for either FLASH or EPI relatively short (e.g. 50 ms). However, for multi-slice imaging, an alternative approach collects a slice-selective projection at a designated location for each repetition and uses it for extracting physiological signals. This is similar to double-slice techniques, but for fMRI, as many slices as desired can be collected, and only one physiological timing slice is needed.

We claim:

1. A functional magnetic resonance imaging method comprising the steps of:
   (a) detecting a physiological timing profile;
   (b) measuring cerebral k-space data;
   (c) ordering the measured cerebral k-space data into a unit cycle based on the detected physiological timing profile;
   (d) estimating corresponding physiological effects for individual k-space data points by non-linear least-square fitting of cerebral k-space data;
   (e) removing the estimated physiological effects from the cerebral k-space data by subtraction, providing cerebral k-space data from which the estimated physical effects have been removed; and
   (f) providing an image from said cerebral k-space data from which the estimated physical effects have been removed.

2. A method of claim 1 in which the physiological timing profile of step (a) is based on respiration.

3. The method of claim 1 in which the physiological timing profile of step (a) is based on cardiac activity.

4. The method of claim 1 in which the physiological timing profile of step (a) is obtained from the phase of the center of a navigator echo in rapid, low flip angle pulsed NMR imaging (FLASH).

5. The method of claim 1 in which the physiological timing profile of step (a) is obtained from the phase of the center k-space point in echo-planar imaging (EPI).

6. The method of claim 1 in which step (a) comprises extracting the physiological timing profile directly from magnetic resonance data.

7. The method of claim 1 in which the non-linear least squares fitting of step (d) is performed as a finite order Fourier series.

8. A functional magnetic resonance imaging method of comprising the steps of:
   (a) detecting a physiological timing profile;
   (b) measuring cerebral k-space data to provide cerebral k-space data;
   (c) ordering the measured cerebral k-space data into a unit cycle based on the detected physiological timing profile;
   (d) estimating effects on individual k-space points resulting from physiological effects by non-linear fitting of cerebral k-space data to provide estimated physiological effects;
   (e) removing the estimated physiological effects from the cerebral k-space data by subtraction of the estimated physiological effects from said k-space data to form image data; and
   (f) forming an image from said image data.

9. The method of claim 1 wherein said physiological timing profile of step (a) is based upon effects selected from the group consisting of respiration and cardiac activity.

10. The method of claim 9 wherein step (a) comprises extracting the physiological timing profile directly from magnetic resonance data.

* * * * *